US008712108B2

(12) United States Patent
Miyahara et al.

(10) Patent No.: US 8,712,108 B2
(45) Date of Patent: Apr. 29, 2014

(54) INFORMATION PROCESSING APPARATUS, INFORMATION OUTPUTTING METHOD AND COMPUTER PROGRAM STORAGE DEVICE

(75) Inventors: Masanori Miyahara, Tokyo (JP); Takehiro Hagiwara, Tokyo (JP); Tomohiro Tsunoda, Tokyo (JP)

(73) Assignee: Sony Corporation, Tokyo (JP)

( * ) Notice: Subject to any disclaimer, the term of this patent is extended or adjusted under 35 U.S.C. 154(b) by 182 days.

(21) Appl. No.: 13/073,400

(22) Filed: Mar. 28, 2011

(65) Prior Publication Data

US 2011/0243392 A1   Oct. 6, 2011

(30) Foreign Application Priority Data

Apr. 6, 2010   (JP) ................................ P2010-087784

(51) Int. Cl.
  *G06K 9/00*   (2006.01)
  *G09B 19/00*   (2006.01)
(52) U.S. Cl.
  USPC ............................ 382/110; 382/224; 434/127
(58) Field of Classification Search
  CPC ..................................... A61B 5/00; A61B 5/15
  USPC ......... 382/100, 103, 106–107, 123, 155, 162, 382/168, 173, 181, 189, 206, 220, 224, 232, 382/254, 274, 276, 294, 305, 312; 600/316, 600/300; 482/4; 434/127; 707/3
  See application file for complete search history.

(56) References Cited

U.S. PATENT DOCUMENTS

| 5,839,901 | A  | * | 11/1998 | Karkanen ...................... 434/127 |
| 6,095,949 | A  | * | 8/2000  | Arai .................................. 482/4 |
| 6,368,272 | B1 | * | 4/2002  | Porumbescu ................. 600/300 |
| 7,959,567 | B2 | * | 6/2011  | Stivoric et al. ................ 600/300 |
| 2003/0208113 | A1 | * | 11/2003 | Mault et al. ................... 600/316 |
| 2009/0112800 | A1 | * | 4/2009  | Athsani ............................. 707/3 |
| 2009/0298021 | A1 | * | 12/2009 | Black et al. .................. 434/127 |

FOREIGN PATENT DOCUMENTS

| JP | 2002-149827 | 5/2002 |
| JP | 2006-171984 | 6/2006 |
| JP | 2007-226621 | 9/2007 |
| JP | 2010-033326 | 2/2010 |
| WO | WO 01/39089 A1 | 5/2001 |

OTHER PUBLICATIONS

U.S. Appl. No. 13/718,132, filed Dec. 18, 2012, Hagiwara, et al.
Extended European Search Report issued Aug. 10, 2011, in Patent Application No. 11160033.4.
Office Action dated Jan. 14, 2014, in Japanese Patent Application No. 2010-087784, filed Apr. 6, 2010.

* cited by examiner

*Primary Examiner* — Seyed Azarian
(74) *Attorney, Agent, or Firm* — Oblon, Spivak, McClelland, Maier & Neustadt, L.L.P.

(57) ABSTRACT

An apparatus, method and computer program storage device cooperate to acquire an image of at least a part of a meal. An analysis is then done on the image to determine a substance in the image. The analysis also considers caloric intake and exercise data and compares the same with a health management model to arrive at a recommendation for a user who consumed the meal. Various optional features include using wireless communications to receive exercise data from sensors, as well as communication related images such as the menu of a restaurant or the location of the restaurant.

19 Claims, 22 Drawing Sheets

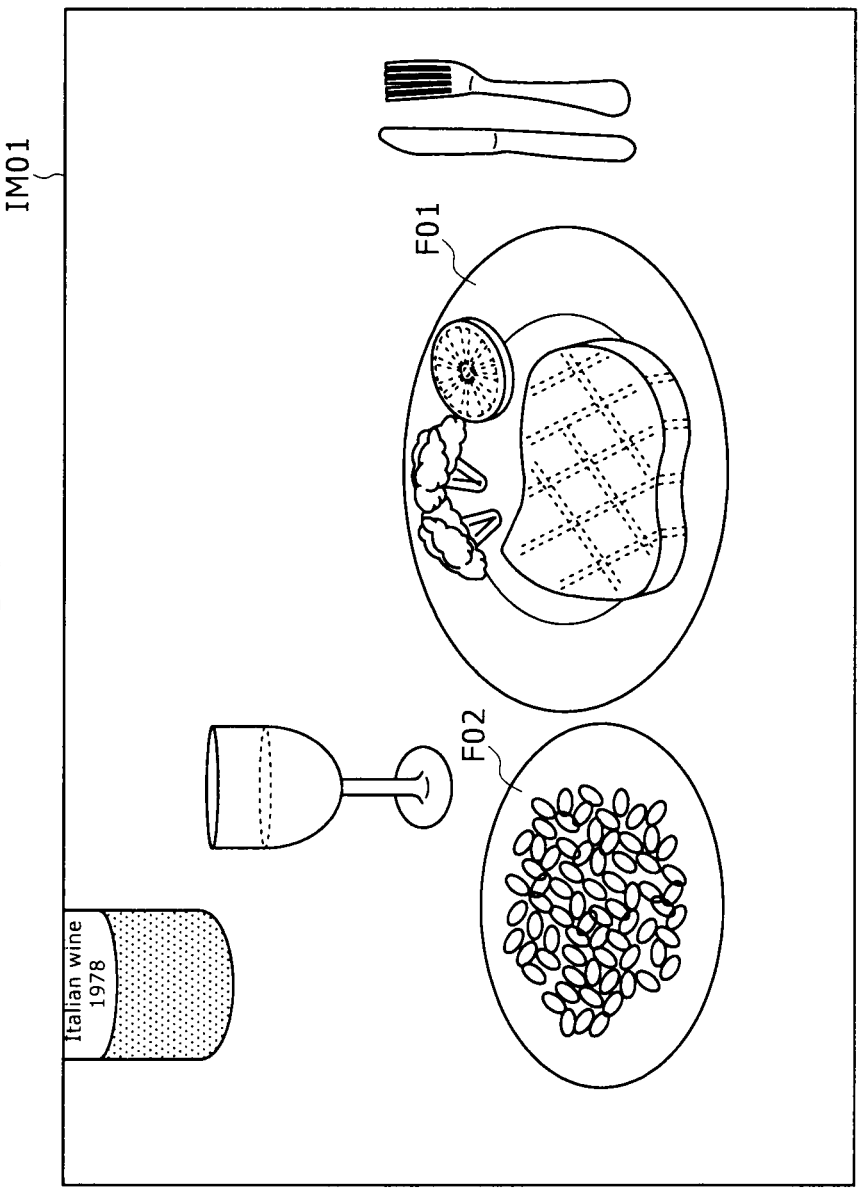

FIG. 10

| MODEL ID | INTAKE AMOUNT | | | | EXERCISE AMOUNT | | EXPLANATION |
| --- | --- | --- | --- | --- | --- | --- | --- |
| | INTAKE ENERGY | CARBO-HYDRATES | FATS | ... | AMOUNT OF MOVEMENT | ENERGY CONSUMPTION | |
| MD1 | 1800kcal | 300g | 120g | ... | 2.0km | 1800kcal | USER A (WHEN PHYSICAL CONDITION IS GOOD) |
| MD2 | 2000kcal | 320g | 100g | ... | 3.0km | 2000kcal | MODEL USER |
| ... | ... | ... | ... | ... | ... | ... | ... |
| MDn | 1200kcal | 180g | 40g | ... | 2.0km | 1800kcal | FOR DIETING |

D7 ↙

MODEL DATA

D6a:

| DATE | INTAKE AMOUNT | | |
|---|---|---|---|
| | INTAKE ENERGY | ... | VITAMIN A |
| March 31, 2010 | 2300kcal | ... | 0.1mg |

D7a:

| MODEL ID | INTAKE AMOUNT | | | EXPLANATION |
|---|---|---|---|---|
| | INTAKE ENERGY | ... | VITAMIN A | |
| MD1 | 1800kcal | ... | 0.6mg | WHEN PHYSICAL CONDITION IS GOOD |

W1

ADVICE FOR HEALTH

VITAMIN A IS SHORT ALTHOUGH THE ENERGY INTAKE AMOUNT IS GREAT. YOU ARE RECOMMENDED TO TAKE A SUPPLEMENT OF VITAMIN A.

| DATE | INTAKE AMOUNT | | | EXERCISE AMOUNT | |
|---|---|---|---|---|---|
| | INTAKE ENERGY | ... | FATS | AMOUNT OF MOVEMENT | ENERGY CONSUMPTION |
| April 1, 2010 | 2000kcal | ... | 180g | 1.0km | 900kcal |

D7b

| MODEL ID | INTAKE AMOUNT | | | EXERCISE AMOUNT | |
|---|---|---|---|---|---|
| | INTAKE ENERGY | ... | FATS | AMOUNT OF MOVEMENT | ENERGY CONSUMPTION |
| MD3 | 1900kcal | ... | 120g | 2.5km | 2000kcal |

W2

ADVICE FOR HEALTH

⚠ YOUR EXERCISE SEEMS INSUFFICIENT FOR MAINTENANCE OF HEALTH AND FIGURE.
YOU ARE RECOMMENDED TO WALK OVER APPROXIMATELY 1.5 KM IN ORDER TO COMBUST EXCESSIVELY TAKEN FATS.

D6a

| DATE | INTAKE AMOUNT | | |
|---|---|---|---|
| | INTAKE ENERGY | ... | VITAMIN A |
| March 31, 2010 | 2300kcal | ... | 0.1mg |

D7a

| MODEL ID | INTAKE AMOUNT | | |
|---|---|---|---|
| | INTAKE ENERGY | ... | VITAMIN A |
| MD1 | 1800kcal | ... | 0.6mg |

W3

ADVICE FOR HEALTH

TO YOU TO WHOM VITAMIN A IS INSUFFICIENT, THE SUPPLEMENT XXX BY YYY PHARMACEUTICAL COMPANY IS EFFECTIVE !

INFORMATION PROCESSING APPARATUS, INFORMATION OUTPUTTING METHOD AND COMPUTER PROGRAM STORAGE DEVICE

BACKGROUND OF THE INVENTION

1. Field of the Invention

This invention relates to an information processing apparatus, an information outputting method and a computer program storage device.

2. Description of the Related Art

It is significant to keep an appropriate balance of eating habits in order to achieve preservation or promotion of the health, prevention of adult diseases, improvement in figure or the like. The Ministry of Health, Labor and Welfare and the Ministry of Agriculture, Forestry and Fisheries of Japan cooperatively decided on and published the "Food Balance Guide" in 2005. Further, the World Health Organization (WHO) and the Food and Agriculture Organization of the United Nations (FAO) reported the "Diet, Nutrition and the Prevention of Chronic Diseases" in 2003. In the "Diet, Nutrition and the Prevention of Chronic Diseases," the range of the target intake regarding nutrients such as carbohydrates, proteins and fats is indicated as a rate to the total energy intake.

However, it is difficult for a general living person to precisely recognize the amount of energy and nutrients taken in from the substance of daily meals and decide whether or not the eating habits of the person itself is appropriate. Therefore, Japanese Patent Laid-Open No. 2003-85289 (hereinafter referred to as Patent Document 1) proposed a system wherein picked up images of the substance of meals are accumulated into a center server such that an advice regarding improvements in the eating habits can be provided from an adviser who accesses the images in order to support to improve eating habits of individuals. Meanwhile, Japanese Patent Laid-Open No. 2003-290155 (hereinafter referred to as Patent Document 2) proposed a system for a health care service wherein food data including the calorie value of food purchased in a store, a restaurant and so forth is acquired, and menus of meals determined in response to the food data and living body information regarding the user are recommended to the user.

SUMMARY OF THE INVENTION

However, according to the system disclosed in Patent Document 1, since the advice for the eating habits relies upon visual observation by the adviser, if no such adviser is available, then the user cannot receive an advice. Meanwhile, according to the system disclosed in Patent Document 2, except for a case in which a user purchases food in a particular store or restaurant which provides food data, appropriate information regarding a recommended menu of a meal is not provided to the user.

Therefore, it is desirable to provide a novel and improved information processing apparatus, information outputting method and program wherein an advice regarding a meal can be provided automatically to a user without being restricted by the place of the meal or the place where the food is purchased.

Accordingly, one embodiment is directed to an apparatus that has a non-transitory computer readable storage device configured to store therein computer readable instructions. A processor is included to acquire an image of at least a part of a meal and when the processor executes the computer readable instructions, the processor sends a request to another device for analyzing the image to recognize a property of the at least part of a meal.

A wireless interface may be included through which the processor sends the request, and through which the processor receives an analysis result from the another device. The wireless interface is configured to receive a wireless signal input from at least one of a heart rate monitor, a pedometer and an accelerometer as input regarding user exercise A display may be included upon which the analysis result is displayed, the analysis result includes an activity recommendation based on a comparison between accumulated caloric intake and accumulated exercise data.

The activity recommendation is based on a comparison of the accumulated caloric intake and accumulated exercise data against a predetermined health management model.

Optionally, the apparatus may include at least one of a heart rate monitor, a pedometer and an accelerometer configured to monitor the accumulated exercise data.

The processor optionally sends at least one of an image of a menu and a text-based version of the menu to the another device for facilitating in the analyzing the image.

A location detector may be included to detect a location of the apparatus when the image of the at least a part of the meal is sent to the another device for facilitating the another device in determining a menu of food items available at eating establishments near the location.

According to another embodiment, a computer may include an interface configured to acquire an image, the image including at least part of a meal. Also an image analysis mechanism is included to analyze the image and recognize a property of the at least part of the meal.

A non-transitory storage device may be included to hold therein a health management model having an accumulated caloric intake component and an exercise component; and a processor may be included to identify at least a caloric quantity associated with the at least part of a meal and update the accumulated caloric intake by including the caloric quantity.

The processor may perform a comparison of the health management model with the accumulated caloric intake and exercise component and produce an activity recommendation based on the comparison, and the interface configured to send the activity recommendation to a terminal from which the image was acquired.

The image analysis mechanism may further be configured to receive at least one of an image of a menu and a text-based version of the menu to assist the image analysis mechanism in recognizing the property. The image analysis mechanism may be configured to receive data describing a location of a terminal that sends the image of the at least a part of the meal to assist the image analysis mechanism in recognizing the property.

In another embodiment a non-transitory computer readable storage device includes an interface configured to receive and store therein downloaded instructions, the downloaded instructions when executed by a computer processor perform a method including acquiring an image of at least a part of a meal; and analyzing with the computer processor the image to recognize a property of the at least part of the meal.

Optionally, the analyzing includes sending a wireless message to another device of the image to recognize the property of the at least part of a meal, and receiving an analysis result from the another device.

The method may also include using at least one of location information and menu information to assist in the analyzing. Similarly, the method may include including accumulated exercise information in the analyzing step; and presenting on a display at least one of a nutrition advice message and a recommended exercise message based on the analysis result.

In another embodiment, a method for analyzing at least part of a meal, includes acquiring an image of at least part of a meal; and analyzing with a computer processor the image to recognize a property of the at least part of the meal as a factor in an analysis result.

Optionally, the analyzing includes including accumulated exercise data as another factor in the analysis result, and comparing the accumulated exercise and the property of the at least part of a meal to a predetermined health management model.

The method may also include sensing at least a portion of the accumulated exercise with at least one of a heart rate monitor, a pedometer and an accelerometer.

With the information processing apparatus, information outputting method and computer program storage device, advice (or advise message) regarding a meal can be provided to a user automatically without being restricted by the place of the meal or the place at which food is purchased.

The above and other features and advantages of the present invention will become apparent from the following description and the appended claims, taken in conjunction with the accompanying drawings.

BRIEF DESCRIPTION OF THE DRAWINGS

FIGS. 4A, 4B and 4C are schematic views showing different examples of an input image to the terminal apparatus of FIG. 2;

FIG. 10 is a view illustrating model data stored in a storage section shown in FIG. 3;

FIGS. 11A, 11B and 11C are views illustrating first, second and third examples, respectively, of output information from an information outputting section shown in FIG. 3;

DETAILED DESCRIPTION OF THE PREFERRED EMBODIMENTS

Figure 1:
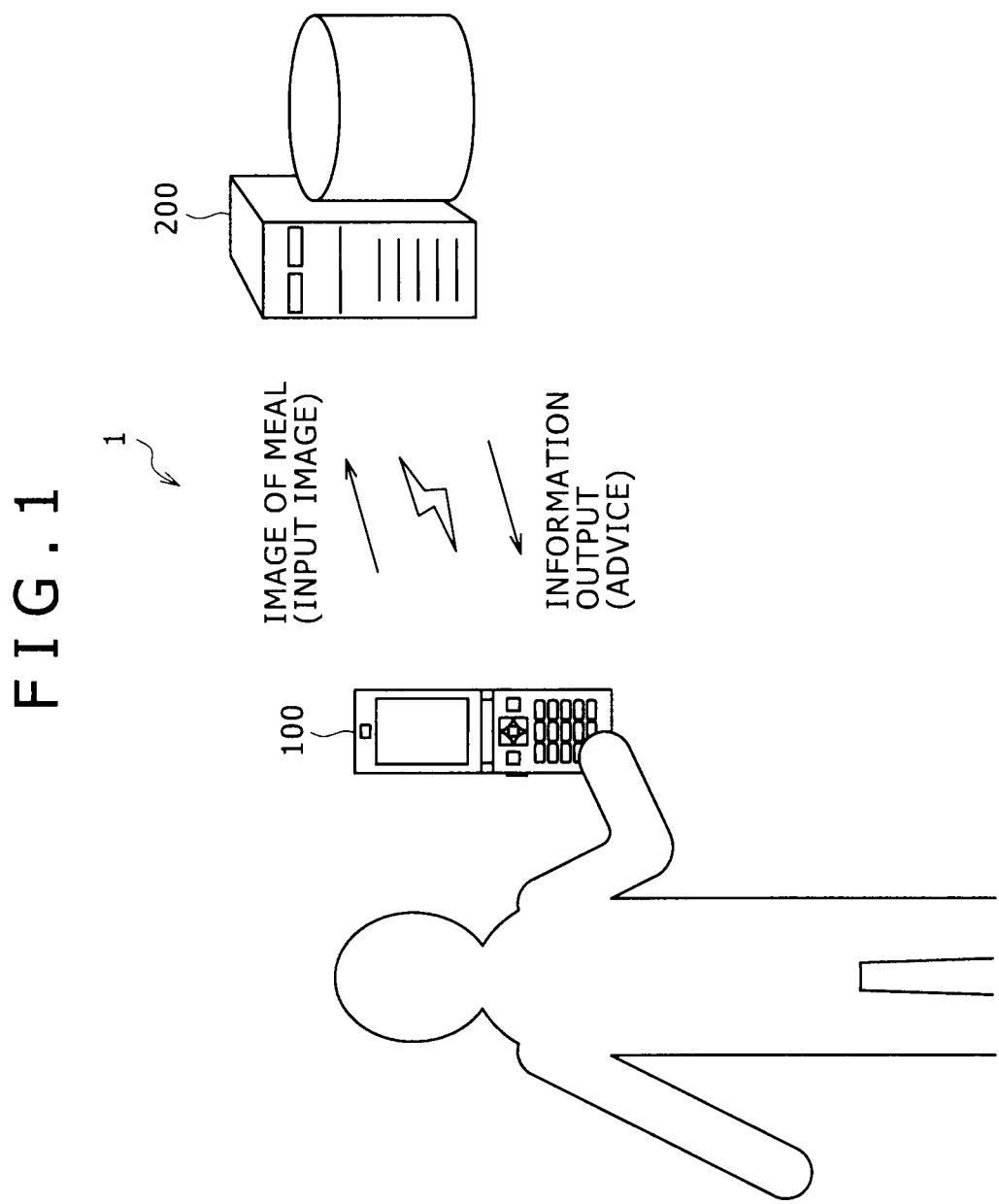
FIG. 1 is a schematic view showing a general configuration of an information processing system to which the present invention is applied.

In the following, preferred embodiments of the present invention are described with reference to the accompanying drawings. It is to be noted, however, that, in the specification and the accompanying drawings, elements or components having substantially like functional configurations are denoted by like reference characters and overlapping description of them is omitted herein to avoid redundancy.

Further, the description of the embodiments is given in the following order.
1. Outline of the System
2. First Embodiment
   2-1. Example of the Configuration of the Terminal Apparatus
   2-2. Example of the Configuration of the Information Processing Apparatus
   2-3. Flow of Processing
   2-4. Summary of the First Embodiment
3. Second Embodiment
   3-1. Example of the Configuration of the Terminal Apparatus
   3-2. Example of the Configuration of the Information Processing Apparatus
   3-3. Flow of Processing
   3-4. Summary of the Second Embodiment 1. Outline of the System First, an outline of a system to which one embodiment of the present invention is applied is described with reference to FIG. 1. FIG. 1 shows a general configuration of an information processing system 1 to which one embodiment of the present invention is applied. The information processing system 1 shown includes a terminal apparatus 100 and an information processing apparatus 200.

The terminal apparatus 100 typically is a portable terminal apparatus having an image pickup function, a display function and a communication function for communicating with the information processing apparatus 200. The terminal apparatus 100 may be a portable telephone terminal, a portable information terminal, a mobile PC (Personal Computer), a digital still camera, a game terminal or a like apparatus. A user would use such a terminal apparatus 100 as just described to pick up an image of the property of a daily meal. Then, the terminal apparatus 100 transmits such picked up images of daily meals to the information processing apparatus 200.

The information processing apparatus 200 has a communication function for communicating with the terminal apparatus 100. The information processing apparatus 200 may be a general purpose computer such as, for example, a PC or a work station or may be an information processing apparatus of any other type such as a digital information appliance or a game machine. The information processing apparatus 200 analyzes input images received from the terminal apparatus 100 to collect data regarding the eating habits of the user. Then, the information processing apparatus 200 uses the collected data to produce information to be advised to the user and transmits the produced information to the terminal apparatus 100.

According to such a configuration of the information processing system 1 as described above, the user can carry the terminal apparatus 100 to a place at which the user takes a meal and supply picked up images of the property of the meal to the information processing apparatus 200 without being restricted by the place. Further, in other embodiments of the present invention hereinafter described, supplemental data like that measured using sensors, or from images, or text is provided in the terminal apparatus 100 and supplied to the information processing apparatus 200 in addition to the picked up images of at least a portion of the substance of the meals.

2. First Embodiment

2-1. Example of the Configuration of the Terminal Apparatus

Figure 2:
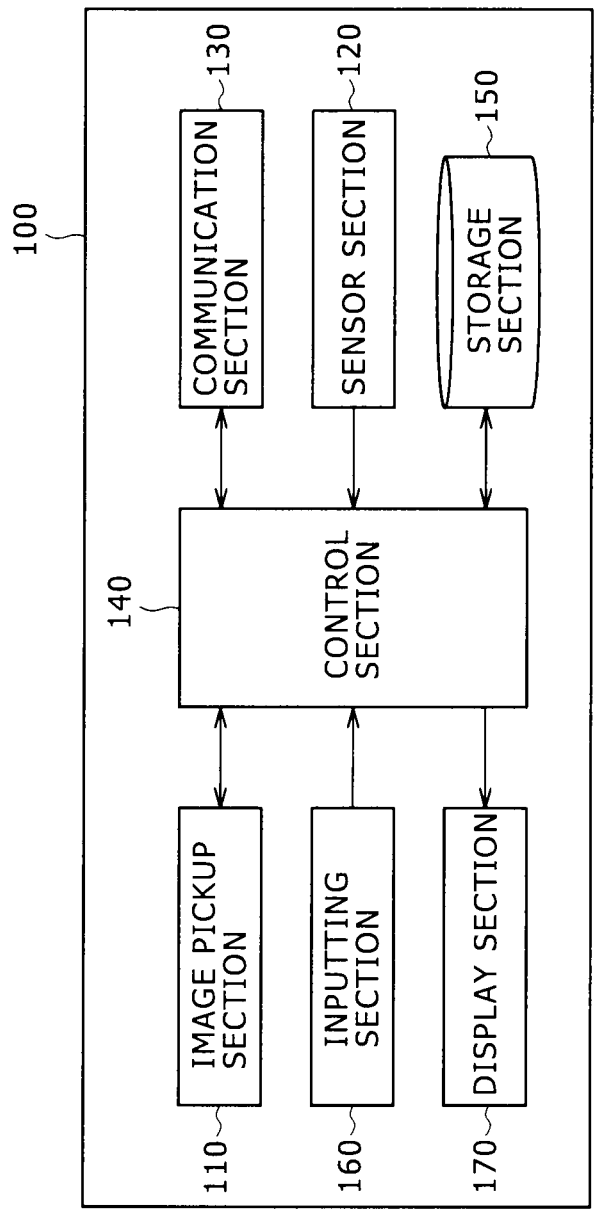
FIG. 2 is a block diagram showing an example of a configuration of a terminal apparatus according to a first embodiment of the present invention.

FIG. 2 shows an example of a configuration of the terminal apparatus 100 according to a first embodiment of the present invention. Referring to FIG. 2, the terminal apparatus 100 includes an image pickup section 110, a sensor section 120, a communication section 130, a control section 140, a storage section 150, an inputting section 160 and a display section 170. While the terminal apparatus 100 is shown as a device, it should be recognized that features of the terminal apparatus may be downloaded software instructions that program a processor in the terminal apparatus 100 to implement the functions described herein.

Image Pickup Section

The image pickup section 110 can be represented as an image pickup module having an image pickup element such as, for example, a CCD (Charge Coupled Device) or CMOS (Complementary Metal Oxide Semiconductor). The image pickup section 110 is used by the user to pick up an image of at least a part of a meal, in an effort to later identify one or more substances (or properties of the substances) that make up the contents of a daily meal. As described hereinabove, images regarding the substance of meals picked up by the image pickup section 110 are transmitted from the terminal apparatus 100 to the information processing apparatus 200.

Sensor Section

The sensor section 120 includes an acceleration sensor for measuring an acceleration caused, for example, by exercise of the user (an example of which is an accelerometer pod placed on the user's shoe, such as is available from POLAR to detect cadence, gait, distance and speed of movement), and a GPS sensor for receiving signals from GPS (Global Positioning System) satellites to detect the position of the user. The sensor section 120 may further include, as additional sensors, living body sensors such as a clinical thermometer, heart rate monitor, and a blood-pressure meter for recognizing a physical condition of the user. The sensor section 120 outputs sensor data including acceleration data obtained by measurement using the acceleration sensor, position data detected using the GPS sensor and living body data measured using the living body sensors to the control section 140. Such sensor data are transmitted from the terminal apparatus 100 to the information processing apparatus 200. At least one of the acceleration data and the position data from among the sensor data is used by the information processing apparatus 200 to calculate the amount of the exercise of the user. Moreover, the sensors are used to determine a cumulative amount of exercise data. It should be noted that the sensors may be wirelessly connected or directly connected to the terminal apparatus 100.

Communication Section

The communication section 130 can be implemented as a communication interface for allowing the terminal apparatus 100 to communicate with the information processing apparatus 200, or even the sensors. The communication section 130 may be a wireless communication interface or may be a wire communication interface. The communication section 130 transmits, for example, an image picked up by the image pickup section 110 to the information processing apparatus 200. Further, the communication section 130 transmits sensor data measured by the sensor section 120 periodically to the information processing apparatus 200. Furthermore, the communication section 130 receives, for example, information transmitted from the information processing apparatus 200 and outputs the received information to the control section 140. Also, the communications section 130 may transmit image data of a menu, or a restaurant name for use by the information processing apparatus 200 in helping to decipher the substance (or property) of the meal contained in the image. Moreover, if the apparatus 200 can detect the contents of items on a restaurant menu, it may help limit the number of candidate foods that it is attempting to detect in the image. Even if a GPS location of the terminal 100 is known to the information processing apparatus 200, the apparatus 200 may use this information to determine candidate restaurants near that location, and then retrieve menu items for those restaurants. The apparatus 200 may also use optical character recognition to directly detect different ingredients contained in a menu of food options.

Control Section

The control section 140 controls the whole functions of the terminal apparatus 100 using a control apparatus such as a CPU (Central Processing Unit). For example, if the inputting section 160 detects a user input for the instruction of image pickup, then the control section 140 instructs the image pickup section 110 to pick up an image. Further, the control section 140 stores sensor data measured periodically by the sensor section 120 into the storage section 150. The control section 140 transmits images of meals picked up by the image pickup section 110 and sensor data stored in the storage section 150 to the information processing apparatus 200 through the communication section 130. Further, if information transmitted from the information processing apparatus 200 is received by the communication section 130, then the control section 140 controls the display section 170 to display the information.

Storage Section

The storage section 150 uses a storage medium such as a hard disk or a semiconductor memory to store programs and data for allowing the terminal apparatus 100 to operate. For example, images of meals and sensor data to be transmitted from the terminal apparatus 100 to the information processing apparatus 200 may be transmitted, after accumulated into the storage section 150, in a cycle of once per several hours or once per one day in response to an instruction of the user to the information processing apparatus 200.

Inputting Section

The inputting section 160 provides a user interface for accepting an instruction or an information input by the user. The user interface provided by the inputting section 160 includes buttons or switches for allowing the user to operate the image pickup section 110. For example, if a release button provided on the terminal apparatus 100 for issuing an instruction to start image pickup is depressed, then the inputting section 160 outputs an operation signal for the instruction to start image pickup to the control section 140.

Display Section

The display section 170 provides a screen interface for outputting information to a screen provided on the terminal apparatus 100. For example, the display section 170 displays information received by the communication section 130 from the information processing apparatus 200 on the screen under the control of the control section 140. The information displayed on the display section 170 includes information regarding nutrients, food or exercise to be recommended to the user, which is produced by the information processing apparatus 200 hereinafter described. Moreover, the display provides the user with useful information relating to how the user's caloric intake and accumulated exercise related to ideal health maintenance plan, as assessed by the information processing apparatus 200.

2-2. Example of the Configuration of the Information Processing Apparatus

Figure 3:
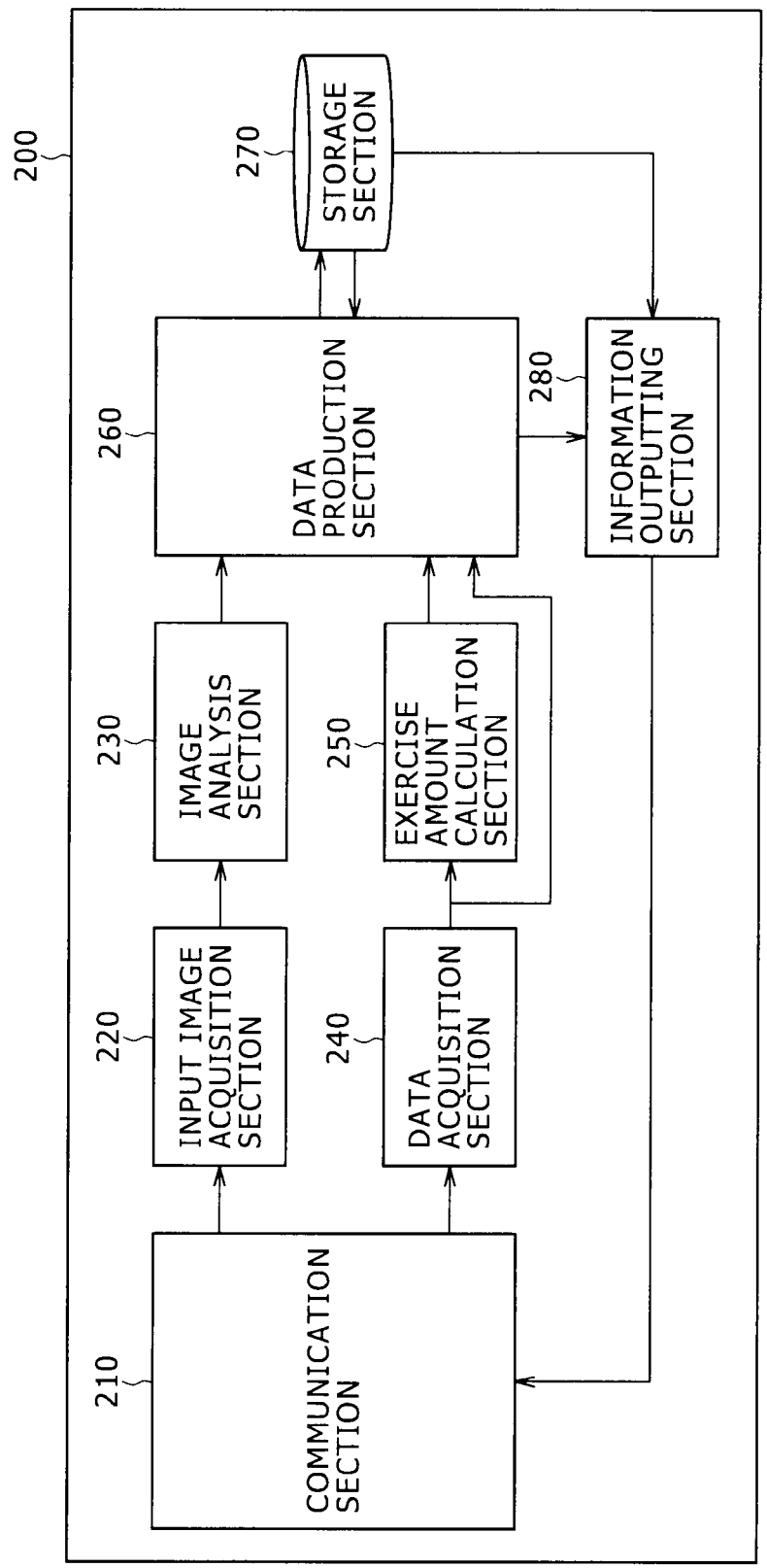
FIG. 3 is a block diagram showing an example of a configuration of an information processing apparatus according to the first embodiment of the present invention.

FIG. 3 is a block diagram showing an example of a configuration of the information processing apparatus 200 according to the present embodiment. Referring to FIG. 3, the information processing apparatus 200 includes a communication section 210, an input image acquisition section 220, an image analysis section 230, a data acquisition section 240, an exercise amount calculation section 250, a data production section 260, a storage section 270 and an information outputting section 280.

Communication Section

The communication section 210 can be implemented as a communication interface for allowing the information processing apparatus 200 to communicate with the terminal apparatus 100. The communication section 210 may be a wireless communication interface or may be a wire communication interface. The communication section 210 receives, for example, images of meals picked up by the terminal apparatus 100 from and sensor data the terminal apparatus 100. Further, the communication section 210 sends, for example, information inputted from the information outputting section 280 to the terminal apparatus 100.

Input Image Acquisition Section

The input image acquisition section 220 acquires an image received from the terminal apparatus 100 by the communication section 210 as an input image. The input image acquired by the input image acquisition section 220 is a picked up image of the substance of a meal by a user of the terminal apparatus 100. The input image acquisition section 220 outputs the acquired input image to the image analysis section 230.

Figure 4C:
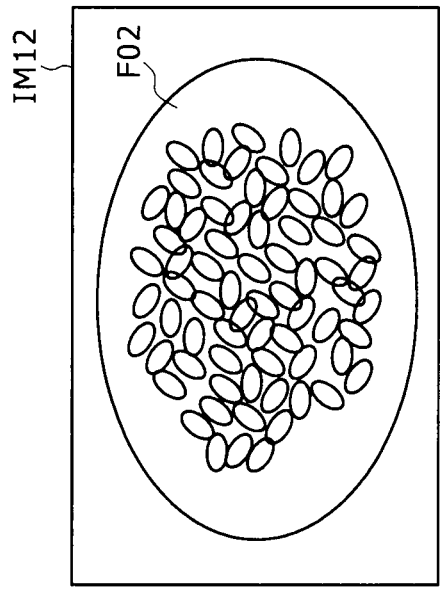
Figure 4B:
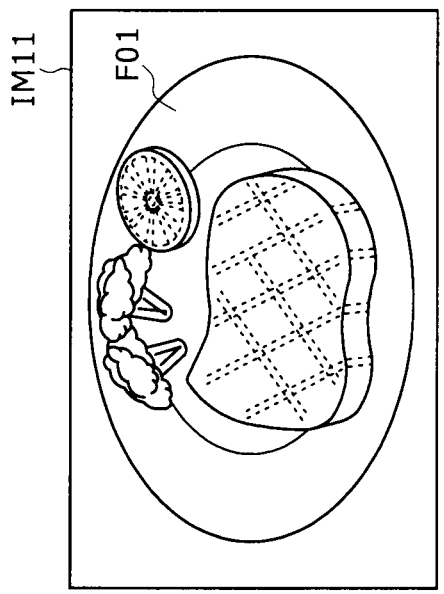

FIGS. 4A to 4C illustrate examples of an input image. Referring first to FIG. 4A, there is shown an input image IM01 as an example picked up using the terminal apparatus 100 by the user. The input image IM01 includes a plate F01 and another plate F02. The plate F01 includes a steak with vegetables. The plate F02 includes rice. In this manner, the input image may be an image representing the entire substance of one meal.

Referring now to FIGS. 4B and 4C, input images IM11 and IM12 as other examples of an image picked up by the user using the terminal apparatus 100 are shown. The input image IM11 includes the plate F01. Meanwhile, the input image IM12 includes the plate F02. In this manner, the input image may be an image picked up for each menu included in one meal. Typically, it is considered that, in the case where an input image picked up for each menu is used, the accuracy in estimation of menus in an image analysis process hereinafter described is higher.

Image Analysis Section

Figure 5:
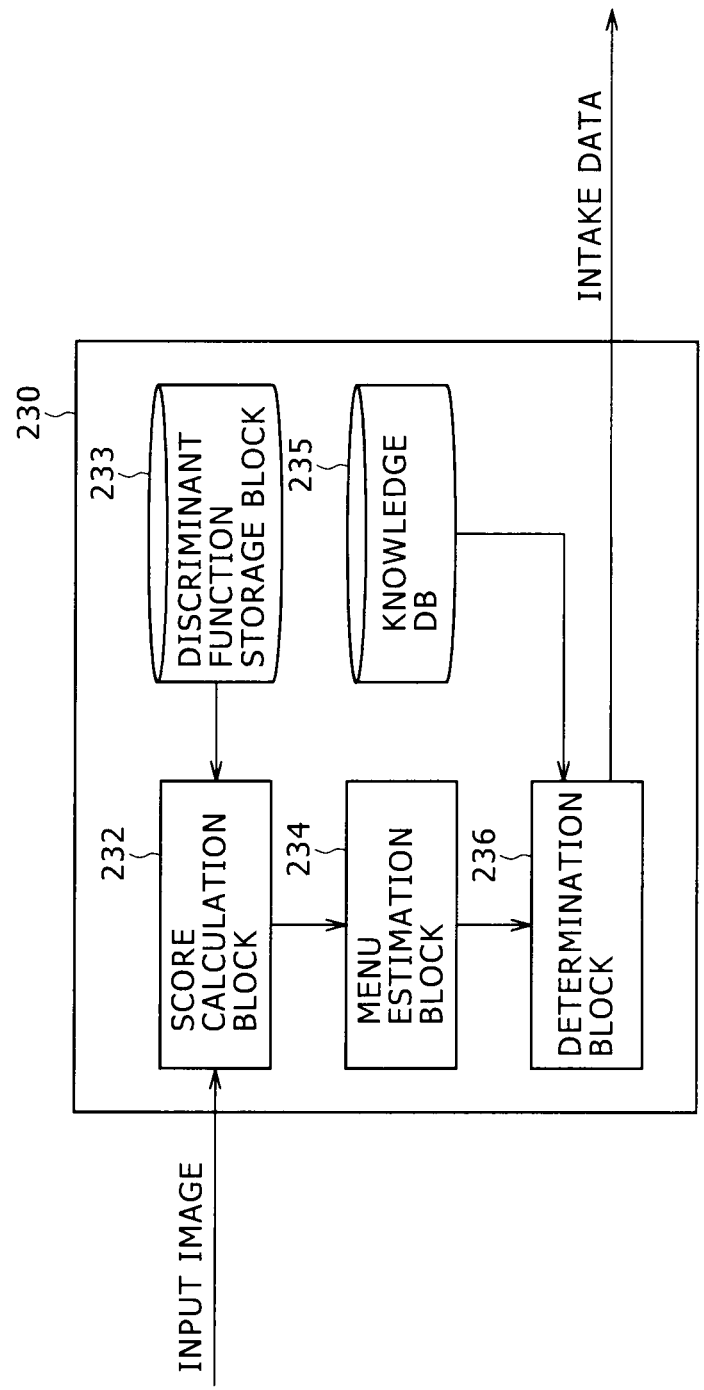
FIG. 5 is a block diagram showing an example of a detailed configuration of an image analysis section shown in FIG. 3.

The image analysis section 230 analyzes an input image acquired by the input image acquisition section 220 to derive the energy of a meal included in the input image and the amount of one or more nutrients included in the meal. FIG. 5 shows an example of a detailed configuration of the image analysis section 230 in the present embodiment. Referring to FIG. 5, the image analysis section 230 includes a score calculation block 232, an discriminant function storage block 233, a menu estimation block 234, a knowledge database (DB) 235 and a determination block 236.

(1) Score Calculation Block

The score calculation block 232 calculates a score for each menu for estimating the menu of a meal included in the input image. A score calculation process by the score calculation block 232 may be a process which uses a discriminant function acquired in advance by publicly known supervised learning such as, for example, leaning based on a support vector machine (SVM) or a neural network or a like method. In this instance, a discriminant function for discriminating a menu of a meal, whose menu type is known, from an image of the meal is acquired by a learning process in advance. Then, if an unknown input image is inputted newly, then the score calculation block 232 applies the discriminant function acquired in advance to the unknown input image.

Figure 6:
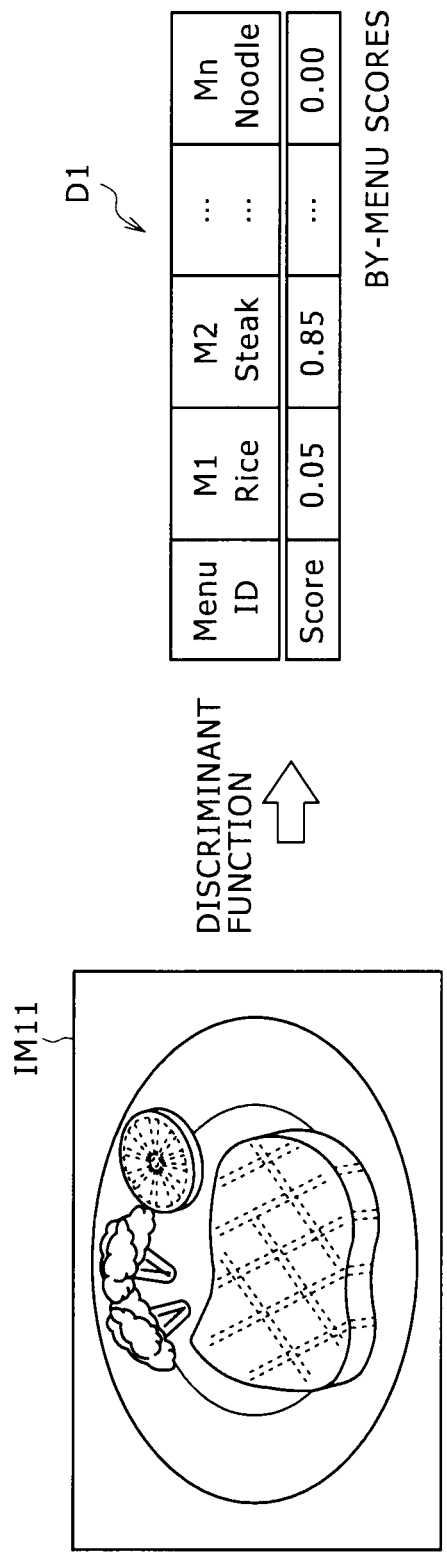
FIG. 6 is a view illustrating a score calculation process executed by a score calculation block shown in FIG. 5.

FIG. 6 illustrates an example of the score calculation process by the score calculation block 232. At a left portion in FIG. 6, the input image IM11 is shown. The score calculation block 232 applies a discriminant function acquired in advance to the input image IM11 to calculate a score for each menu regarding the input image IM11. The score calculated here represents a probability that the input image IM11 is an image indicating a menu discriminated from each menu ID. For example, the score regarding the menu ID=M1 ("Rice") in a right portion in FIG. 6 is 0.05; the score regarding the menu ID=M2 ("Steak") is 0.85; and the score menu ID=Mn ("Noodle") is 0.00. The score calculation block 232 outputs such by-menu scores D1 to the menu estimation block 234.

(2) Discriminant Function Storage Block

The discriminant function storage block 233 has the discriminant function described hereinabove with reference to FIG. 6 stored therein in advance using a storage medium. The discriminant function storage block 233 may be implemented using a storage medium physically same as that of the knowledge DB 235 or the storage section 270 hereinafter described.

(3) Menu Estimation Block

The menu estimation block 234 estimates the menu of the meal indicated in the input image based on the by-menu scores calculated by the score calculation block 232. In the present embodiment, the menu estimation block 234 estimates a menu of a meal corresponding to a menu ID which exhibits the highest one of the by-menu scores calculated by the score calculation block 232 as the menu of the meal indicated by the input image. For example, in the example of FIG. 6, the by-menu score calculated with regard to the input image IM11 exhibits the highest value at the menu ID=M2 ("Steak"). Therefore, the menu estimation block 234 estimates that the input image IM11 is an image picked up from a steak as a menu of the meal. It is to be noted that, in a second embodiment hereinafter described, the menu estimation block 234 carries out estimation of a menu based further on other supplemental data in addition to the by-menu scores.

(4) Knowledge DB

Figure 7:
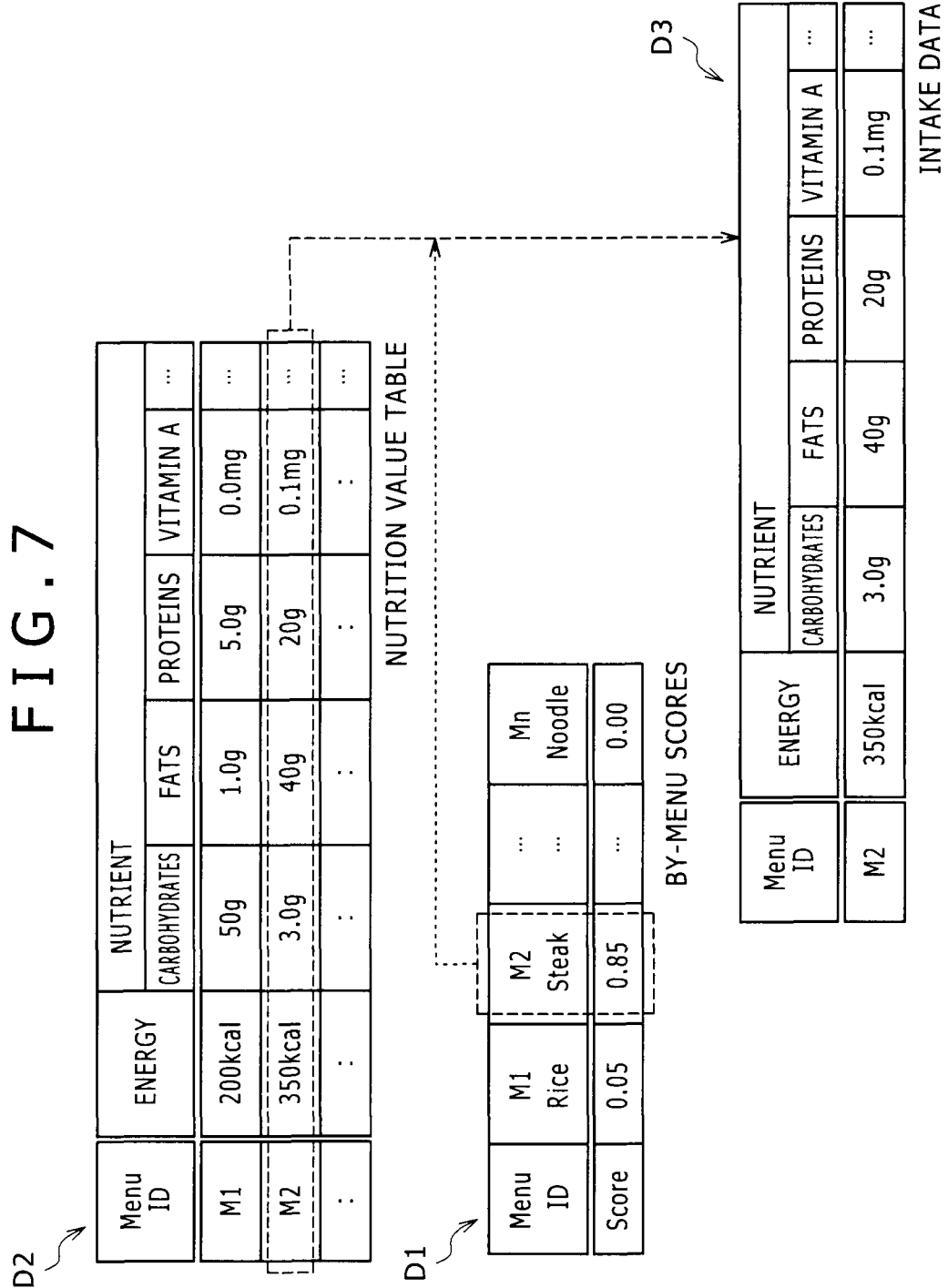
FIG. 7 is a view illustrating an intake data determination process executed by a determination block shown in FIG. 5.

The knowledge DB 235 stores knowledge to be used for determination of a menu by the image analysis section 230 using a storage medium. In the present embodiment, the knowledge DB 235 has such a nutrition value table D2 as illustrated in FIG. 7. The nutrition value table D2 includes records individually corresponding to menu items M1 to Mn of the by-menu scores D1 illustrated in FIG. 6. Further, data items of the nutrition value table D2 represent energy corresponding to the individual menus and the quantity of one or more nutrients included in the menus. In the example of FIG. 7, the second column of the nutrition value table D2 represents the energy or calorie value; the third column the quantity of carbohydrates; the fourth column the quantity of fats; the fifth column the quantity of proteins; and the sixth column the quantity of the vitamin A. The values of the data items of the nutrition value table D2 may be defined, for example, individually for each user for one menu. In this instance, a quantity corresponding to an average amount of a meal to be taken in by each individual user is defined in the nutrition value table D2. Alternatively, the value of each data item of the nutrition value table D2 may be defined by one record common to a plurality of users regarding one menu. In this instance, a quantity corresponding to a general amount of a meal which does not rely upon the user is defined in the nutrition value table D2.

(5) Determination Block

The determination block 236 uses the nutrition value table D2 of the knowledge DB 235 to determine the value of energy and the quantity of one or more nutrients corresponding to a menu estimated by the menu estimation block 234. The data values determined by the determination block 236 are outputted as intake data or eating amount data representative of the energy and the quantity of nutrients taken in by the user to the data production section 260.

FIG. 7 illustrates an intake data determination process by the determination block 236 in the present embodiment. At an upper stage in FIG. 7, the nutrition value table D2 described hereinabove stored in advance in the knowledge DB 235 is shown. At an intermediate stage in FIG. 7, by-menu scores D1 calculated by the score calculation block 232 are illustrated. In the by-menu scores D1, the menu ID=M2 (hereinafter referred to as menu M2) exhibits the highest score. Therefore, the menu estimation block 234 estimates that the menu M2, that is, a steak, is included in the input image as described hereinabove. Then, the determination block 236 searches the nutrition value table D2 for a record corresponding to the menu M2. Consequently, the determination block 236 uses the record corresponding to the menu M2 acquired from the nutrition value table D2 to determine the values of data items of intake data D3. In the example of FIG. 7, the values of the data items of the intake data D3 are determined, using the values of the record corresponding to the menu M2 as they are, such that energy=350 kcal, carbohydrates=3.0 g, fats=40 g, proteins=20 g, vitamin A=0.1 mg and so forth.

Data Acquisition Section

The data acquisition section 240 acquires sensor data received from the terminal apparatus 100 by the communication section 210. In the present embodiment, the sensor data acquired from the data acquisition section 240 represent a series of positions, accelerations, body temperatures and so forth in a time series detected periodically regarding the user who carries the terminal apparatus 100. The data acquisition section 240 outputs, from among the sensor data, the position data and the acceleration data to the exercise amount calculation section 250. Further, the data acquisition section 240 outputs the living body data of the body temperature and so forth to the data production section 260.

Exercise Amount Calculation Section

The exercise amount calculation section 250 uses the sensor data inputted from the data acquisition section 240 to calculate the amount of exercise carried out by the user within a period from the preceding reception of sensor data to the current reception of sensor data.

Figure 8:
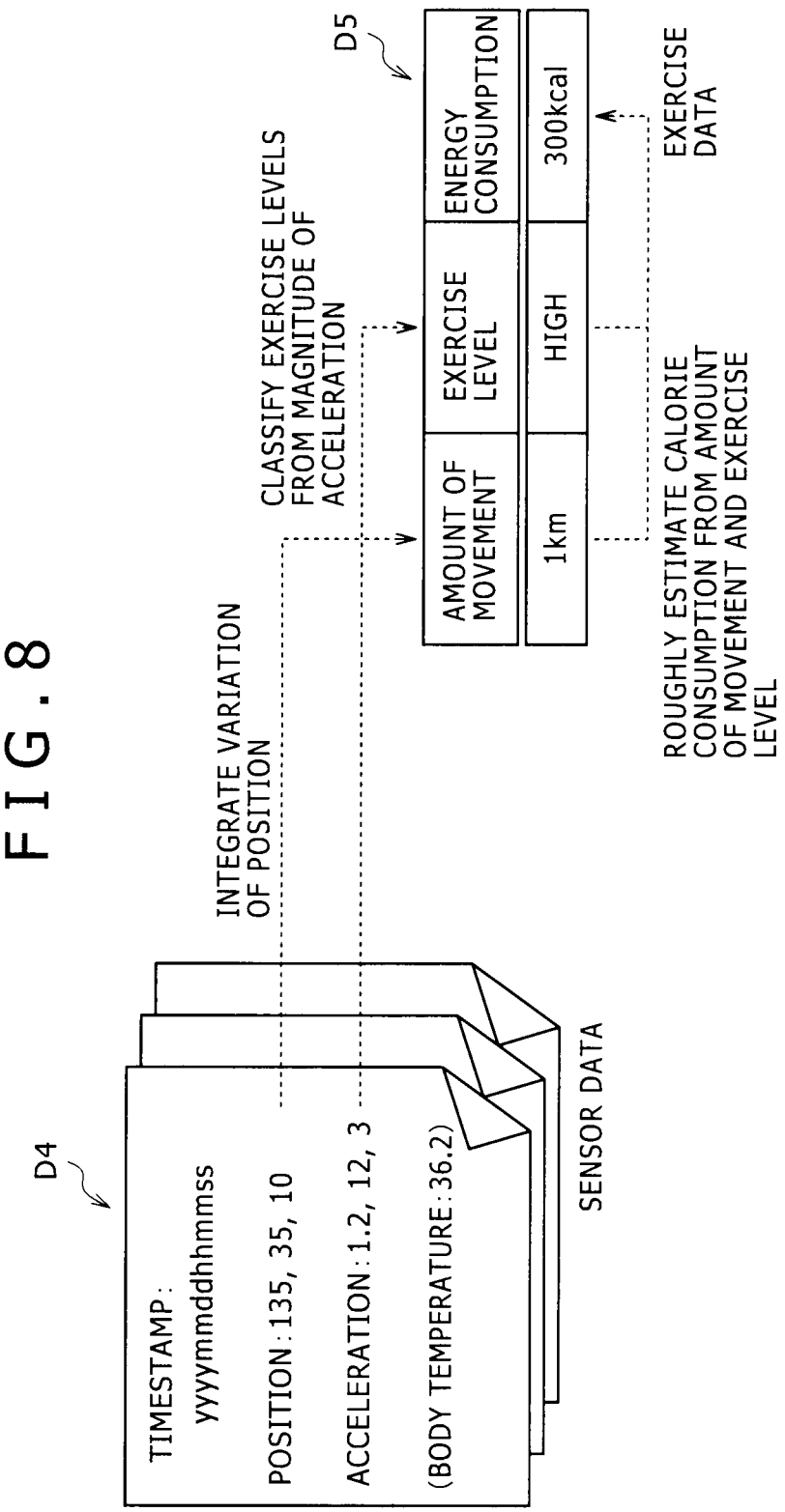
FIG. 8 is a view illustrating an exercise amount calculation process executed by an exercise amount calculation section shown in FIG. 3.

FIG. 8 illustrates an exercise amount calculation process by the exercise amount calculation section 250 in the present embodiment. At a left portion in FIG. 8, a series of sensor data D4 are indicated. Each sensor data D4 includes a timestamp, position data, acceleration data and living body data indicative of a value of the body temperature. The exercise amount calculation section 250 principally uses the timestamp, position data and acceleration data to calculate the exercise amount.

At a right portion in FIG. 8, exercise data D5 calculated by the exercise amount calculation section 250 are illustrated. The exercise data D5 have three data items including the amount of movement, the exercise level and the energy consumption. In the exercise amount calculation process, the exercise amount calculation section 250 first calculates a variation between the positions of the user which corresponds to a difference between two position data of the sensor data which are adjacent each other on the time axis. Then, the exercise amount calculation section 250 integrates the variations of the position of the user in the series of sensor data D4 to calculate the amount of movement of the user in a period corresponding to the series of sensor data D4. Further, the exercise amount calculation section 250 compares, for example, an average value of the acceleration of the user within the period with a predetermined threshold value to classify the exercise level of the user into three levels of "high," "middle" and "low." For example, "high" may be an exercise level corresponding to running; "middle" may be an exercise level corresponding to walking; and "low" may be an exercise level corresponding to a stationary state. Then, the exercise amount calculation section 250 calculates, from the calculated amount of movement and exercise level, the rough estimation value Ec [kcal] of the energy consumption of the user, for example, in accordance with the following expression:

$$E_C = \lambda \cdot w_{user} \cdot D \quad (1)$$

where $\lambda$ is an energy consumption coefficient which relies upon the required time and the exercise level, $w_{user}$ is the body weight of the user, and D is the amount of movement [km].

The exercise amount calculation section 250 outputs exercise data D5 representative of the amount of exercise of the user calculated in this manner to the data production section 260.

Data Production Section

The data production section 260 produces life data including intake data representative of a result of an analysis by the image analysis section 230 and exercise data representative of a result of calculation by the exercise amount calculation section 250.

Figure 9:
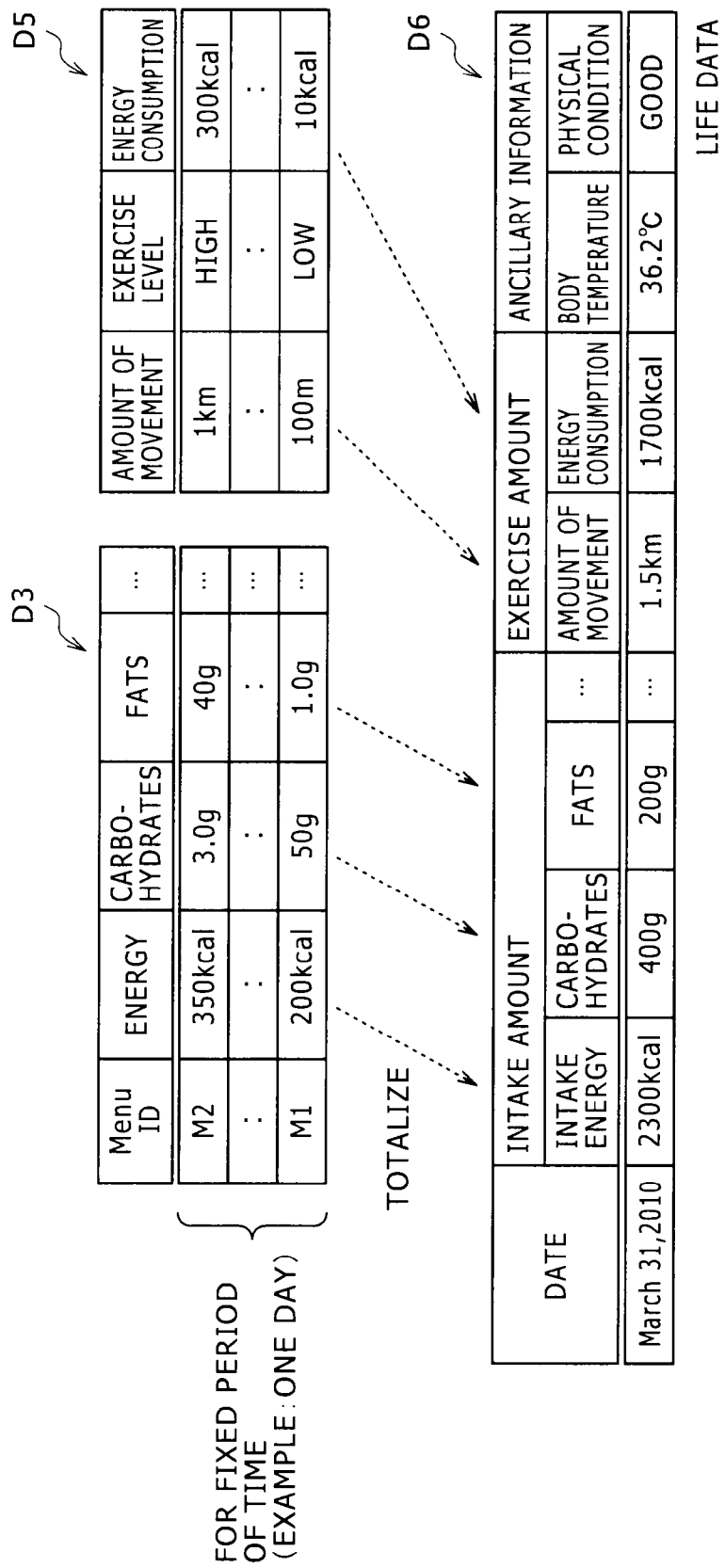
FIG. 9 is a view illustrating a life data production process executed by a data production section shown in FIG. 3.

FIG. 9 illustrates a life data production process by the data production section 260 in the present embodiment.

At a left upper portion in FIG. 9, a plurality of intake data D3 outputted from the image analysis section 230 over a fixed period of time such as, for example, one day, are illustrated. For example, if the terminal apparatus 100 transmits one input image for each of three meals in the morning, daytime and evening, then the intake data D3 for one day include three records. The data production section 260 totalizes the values of the individual data items of the intake data D3 over such a fixed period of time to calculate the data values regarding the intake amounts of the life data. In the example of FIG. 9, as the intake amounts in life data D6 on Mar. 31, 2010 as an example, the values of the intake energy=2,300 kcal, carbohydrates=400 g and fats=220 g are indicated.

At a right upper portion in FIG. 9, a plurality of exercise data D5 outputted from the exercise amount calculation section 250 over a fixed period of time such as, for example, one day, are illustrated. The data production section 260 totalizes the values of the amount of exercise and the energy consumption from among the data items of the exercise data D5 over such a fixed period of time to calculate the data value regarding the amount of exercise from among the life data. In the example of FIG. 9, as the exercise amounts in the exercise data D5 on Mar. 31, 2010 as an example, the values of the amount of movement=1.5 km and energy consumption=1, 700 kcal are indicated.

Further, the data production section 260 attaches supplemental information of the body temperature, a physical condition of the user received from the terminal apparatus 100 as supplemental information to the life data D6. The value of the body temperature in the life data D6 may be, for example, an average value of the body temperature values included in the sensor data acquired by the data acquisition section 240 over the fixed period of time. Meanwhile, the value of the physical condition in the life data D6 may be one of two different values representative of "good" and "not good" estimated from the living body data such as the body temperature. Alternatively, the user may expressly input its physical condition at an arbitrary point of time using the inputting section 160 of the terminal apparatus 100.

The data production section 260 stores the life data produced in this manner into the storage section 270 and outputs the life data to the information outputting section 280.

Storage Section

The storage section 270 stores model data to be compared with the life data described hereinabove produced by the data production section 260 using a storage medium. The model data represent target values regarding the energy of meals to be taken in by the user over a fixed period of time, the quantity of one or more nutrients included in the meals and the amount of exercise to be carried out by the user.

FIG. 10 illustrates the model data stored in the storage section 270 in the present embodiment. Referring to FIG. 10, the storage section 270 stores a plurality of types of model data D7 from a model ID=MD1 to a model ID=MDn.

As the model data whose model ID=MD1 (such model data are hereinafter referred to as model MD1) from among the model data D7, the intake energy=1,800 kcal, intake amount of carbohydrates=300 g, intake amount of fats=120 g, amount of movement=2.0 km and energy consumption=1,800 kcal are stored. The model MD1 is, for example, model data produced from life data in the past regarding the user. The model MD1 may be model data of, for example, a particular day in which the physical condition of the user is good. Alternatively, the model MD1 may be averaged data of daily life data within a period within which the physical condition of the user is good.

Meanwhile, as the model MD2, the intake energy=2,000 kcal, intake amount of carbohydrates=320 g, intake amount of fats=100 g, amount of movement=3.0 km and energy consumption=2,000 kcal are stored. The model MD2 may be, for example, model data representative of life of an ideal model user. The data values of the model MD2 can be defined in advance, for example, based on nutritional knowledge.

Further, as the model MDn, the intake energy=1,200 kcal, intake amount of carbohydrates=180 g, intake amount of fats=40 g, amount of movement=2.0 km and energy consumption=1,800 kcal are stored. The model MDn is model data which are compared with life data, for example, in the case where the user intends weight reduction or dieting.

The storage section 270 selectively outputs one of such plural types of model data D7 as described above to the information outputting section 280 in response to an instruction of the user of the terminal apparatus 100.

Information Outputting Section

The information outputting section 280 outputs information regarding a nutrient, food or exercise to be recommended to the user based on the comparison between one of the model data designated by the user from among the plural types of model data described above and the life data of the user. The information outputted from the information outputting section 280 is transmitted to the terminal apparatus 100 through the communication section 210 and displayed on the screen of the display section 170 of the terminal apparatus 100. The information outputted from the information outputting section 280 may be, for example, information regarding an advice from a point of view of the health, figure and so forth concerning the eating habits of the user. For example, if it is decided based on a comparison between the model data and the life data that some nutrient is short to the user, then the information outputting section 280 may output the short nutrient or information regarding food or a menu of a meal which includes the nutrient. Further, for example, if it is decided based on the result of comparison between the model data and the life data that the consumption amount of energy is short, then the information outputting section 280 may output information for recommending exercise to the user. Still further, for example, the information outputting section 280 may output an advertisement regarding a nutrient, food or exercise decided to be recommended to the user based on the comparison between the model data and the life data.

Figure 11A:

FIG. 11A illustrates a first example of the output information outputted from the information outputting section 280.

At an upper stage in FIG. 11A, life data D6a and model data D7a for being compared with each other by the information outputting section 280 are illustrated. The life data D6a are life data on Mar. 31, 2010, and represent that, on the date, the user took in the energy of 2,300 kcal and the vitamin A of 0.1 mg. On the other hand, the model data D7a are model data regarding the model MD1 and indicate that the energy taken in when the physical condition of the user was good in the past is 1,800 kcal and the quantity of the vitamin A is 0.6 mg. The information outputting section 280 decides based on comparison between such life data D6a and model data D7a as described above and outputs information for recommending the user to take in vitamin A. As a result, at a lower stage in FIG. 11A, an information display screen image W1 as an example displayed on the screen of the terminal apparatus 100 is shown. The information display screen image W1 is a screen image which displays a message which recommends the user to take in vitamin A.

FIG. 11B illustrates a second example of the output information outputted from the information outputting section 280.

At an upper stage in FIG. 11B, life data D6b and model data D7b for being compared with each other by the information outputting section 280 are illustrated. The life data D6b are life data on Apr. 1, 2010, and indicate that, on the day, the user took in the energy of 2,000 kcal and fats of 180 g and that the user carried out exercise of the amount of movement of 1.0 km and the energy consumption of 900 kcal. On the other hand, the model data D7b are model data regarding the model MD3, and indicates that, in the model, intake of the energy of 1,900 kcal and fats of 120 g per one day and exercise of the amount of movement of 2.5 km and the energy consumption of 2,000 kcal are recommendable. The information outputting section 280 recognizes based on the comparison between the life data D6*b* and the model data D7*b* that fats are taken in excessively by the user and that exercise by the user is insufficient. Therefore, the information outputting section 280 outputs information for notifying the user that fats are taken in excessively and that exercise is recommendable. As a result, such an information display screen image W2 as shown at a lower stage in FIG. 11B is displayed on the screen of the terminal apparatus 100.

Figure 11C:
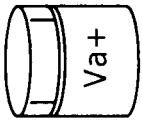

FIG. 11C illustrates a third example of the output information outputted from the information outputting section 280.

At an upper stage in FIG. 11C, the life data D6*a* and the model data D7*a* for being compared with each other by the information outputting section 280 are illustrated again. The information outputting section 280 may output, based on the comparison between the life data D6*a* and the model data D7*a*, an advertisement regarding vitamin A which is a nutrient to be recommended to the user in place of such information as illustrated in FIG. 11A. For example, on such an information display screen image W3 as shown at a lower stage in FIG. 11C, an advertisement regarding a supplement for taking in vitamin A is presented to the user. Or, in place of the advertisement of a supplement, for example, an advertisement regarding food which includes vitamin A, an advertisement of a store or a restaurant which provides food which includes vitamin A or the like may be presented on the information display screen image W3. Further, if it is decided that the consumption amount of energy by the user is short as in the case of the example of FIG. 11B, then an advertisement regarding exercise such as, for example, an advertisement regarding a sports club or a fitness gym may be presented.

2-3. Flow of Processing

Figure 12:
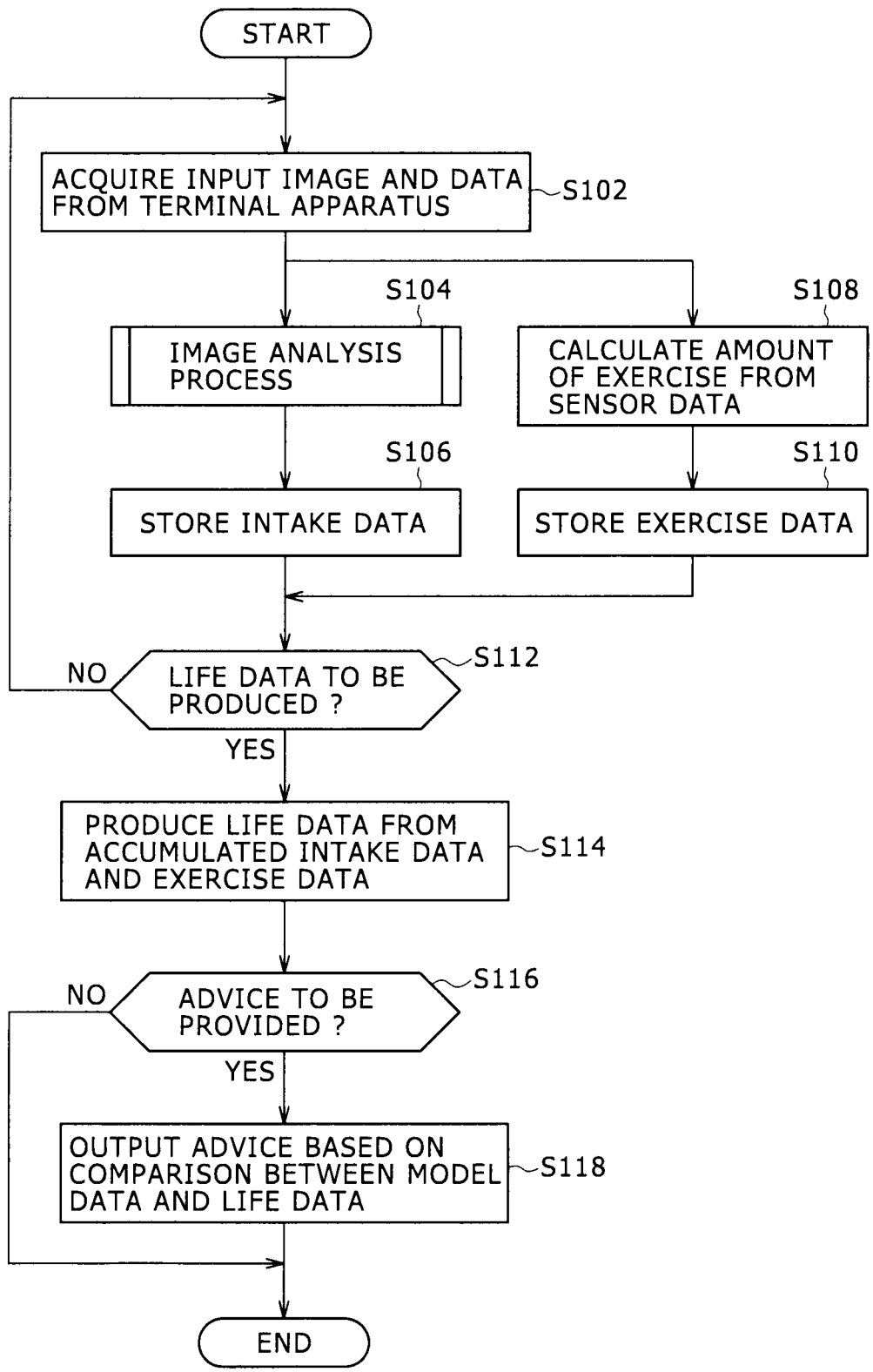
FIG. 12 is a flow chart illustrating an example of a flow of an information outputting process carried out by the information processing apparatus of FIG. 3.

FIG. 12 illustrates an example of a flow of an information outputting process by the information processing apparatus 200 according to the present embodiment.

Referring to FIG. 12, the input image acquisition section 220 of the information processing apparatus 200 first acquires an input image from the terminal apparatus 100 through the communication section 210. Further, the data acquisition section 240 of the information processing apparatus 200 acquires sensor data from the terminal apparatus 100 through the communication section 210 at step S102.

Then, the image analysis section 230 of the information processing apparatus 200 carries out, at step S104, an image analysis process, which is hereinafter described with reference to FIG. 13, regarding the input image acquired by the input image acquisition section 220. Then, the storage section 270 stores intake data inputted from the image analysis section 230 as a result of the image analysis process at step S106.

Further, the exercise amount calculation section 250 of the information processing apparatus 200 calculates the amount of exercise by the user using the sensor data acquired by the data acquisition section 240 at step S108. Then at step S110, the storage section 270 stores the exercise data calculated by the exercise calculation section 250 indicative of the amount of exercise carried out by the user.

Then at step S112, the data production section 260 decides whether or not life data should be produced. For example, if the point of time of the processing corresponds to a timing of production of life data after every fixed period of time such as, for example, one day, then the data production section 260 determines to produce life data. In this instance, the processing advances to step S114. On the other hand, if life data should not be produced, then the processing advances to step S102 so that the acquisition of an input image and sensor data and the storage of intake data and exercise data are repeated.

At step S114, the data production section 260 produces life data from the intake data and the exercise data over a fixed period of time accumulated in the storage section 270 at step S114. Then, the information outputting section 280 decides at step S116 whether or not an advice should be provided to the user. Here, if no advice should be provided to the user, then the step S118 is skipped. On the other hand, if an advice should be provided to the user, then the information outputting section 280 outputs, at step S118, information including such an advice to the user of the terminal apparatus 100 as illustrated in FIG. 11A, 11B or 11C based on comparison between the model data (e.g., health management model, which includes one or more of nutrition, caloric intake and exercise as factors) and the life data.

Figure 13:
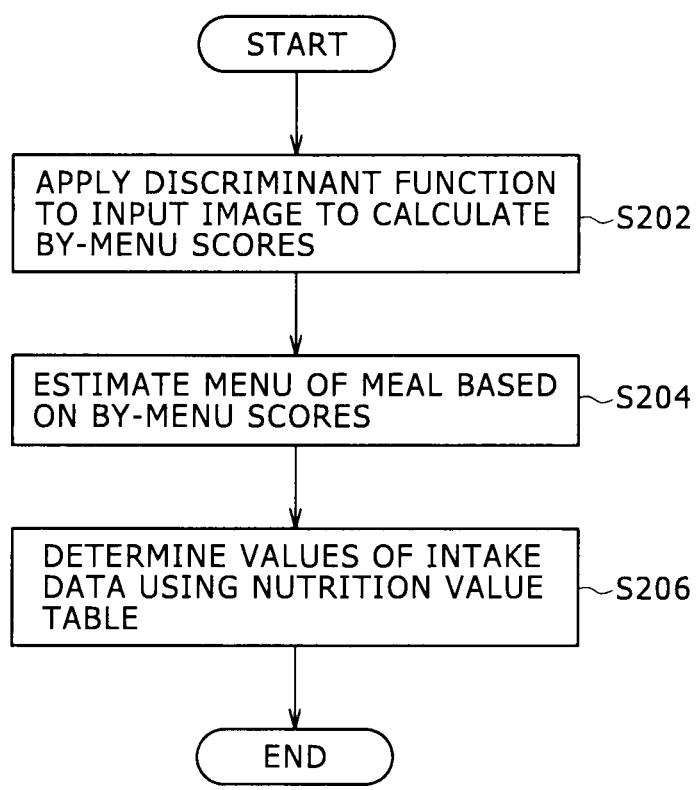
FIG. 13 is a flow chart illustrating an example of a flow of an image analysis process of FIG. 12.

FIG. 13 illustrates an example of a flow of an image analysis process by the image analysis section 230 of the information processing apparatus 200 according to the present embodiment.

Referring to FIG. 13, the score calculation block 232 of the image analysis section 230 first applies a discriminant function acquired by a learning process in advance to the input image to calculate by-menu scores at step S202. Then, the menu estimation block 234 estimates, at step S204, a menu of a meal included in the input image based on the by-menu scores calculated by the score calculation block 232. Then, the determination block 236 searches, at step S206, the records of a nutrition value table corresponding to the estimated menu estimated by the menu estimation block 234 to determine values of the intake data regarding the menu of the meal included in the input image.

2-4. Summary of the First Embodiment

The first embodiment of the present invention is described above with reference to FIGS. 1 to 13. According to the present embodiment, based on comparison between model data representative of target values regarding the energy of a meal, the quantity of one or more nutrients included in the meal and the amount of exercise and life data including a result of analysis of a picked up input image of the substance of the meal and the amount of exercise carried out by the user, an advice regarding eating habits is provided to the user. Consequently, the advice regarding the meal can be provided to the user without being restricted by the place of the meal or the place of purchase of the food.

Further, in the present embodiment, the value of the intake energy and the quantity of taken in nutrients included in the life data described above are determined by estimating a menu of a meal from an input image and acquiring nutritive value data representative of values of the energy and the quantity of nutrients corresponding to the menu of the meal. Accordingly, the user can receive an advice regarding a meal only by picking up an image of a meal using a portable terminal having an image pickup function such as a portable telephone set with a camera or the like.

Further, in the present embodiment, an advice regarding eating habits is obtained by comparing model data of one model designated by the user from among a plurality of types of model data and life data of the user. For example, model data of one of the plural types are data produced from life data in the past regarding the user. Consequently, the tendency of the life of the user in the past when the user was healthy and the life of the user at present can be compared with each other readily. Further, an advice regarding eating habits such as, for example, an advice based on comparison between a model representative of a tendency of an ideal life and the life at present or an advice intended for a particular object such as dieting can be provided after it is adapted in accordance with a desire of the user.

Further, in the present embodiment, an example of an advice regarding eating habits is an advice regarding a nutrient decided to be insufficient to the user or food or a menu of a meal which includes the nutrient. Further, in the present embodiment, another advice regarding eating habits is an advice of recommending the user to carry out exercise in the case where it is decided that the amount of energy consumption is short. In particular, according to the present embodiment, various advices such as an advice regarding exercise derived from eating habits or an advice regarding eating habits derived from a situation of exercise of the user can be provided to the user.

Further, in the present embodiment, an advertisement regarding a nutrient, food or exercise to be recommended to the user can be provided to the user in place of an advice regarding eating habits. Accordingly, for example, an enterprise or a shop can precisely grasp needs of users from a situation of eating habits of the users and provide advertisements effective for being solicited to the individual users.

3. Second Embodiment

In the first embodiment, a discriminant function acquired by a learning process in advance is used for estimation of a menu of a meal based on an input image. In the learning process, the accuracy in estimation of a menu can be raised by supervised learning using a large number of teacher images which are images of meals with regard to which types of menus are known. However, cooked meals generally exhibit various outward appearances. Therefore, also it is useful to determine intake data supplementally using information other than an input image as in a second embodiment of the present invention described below.

3-1. Example of the Configuration of the Terminal Apparatus

Figure 14:
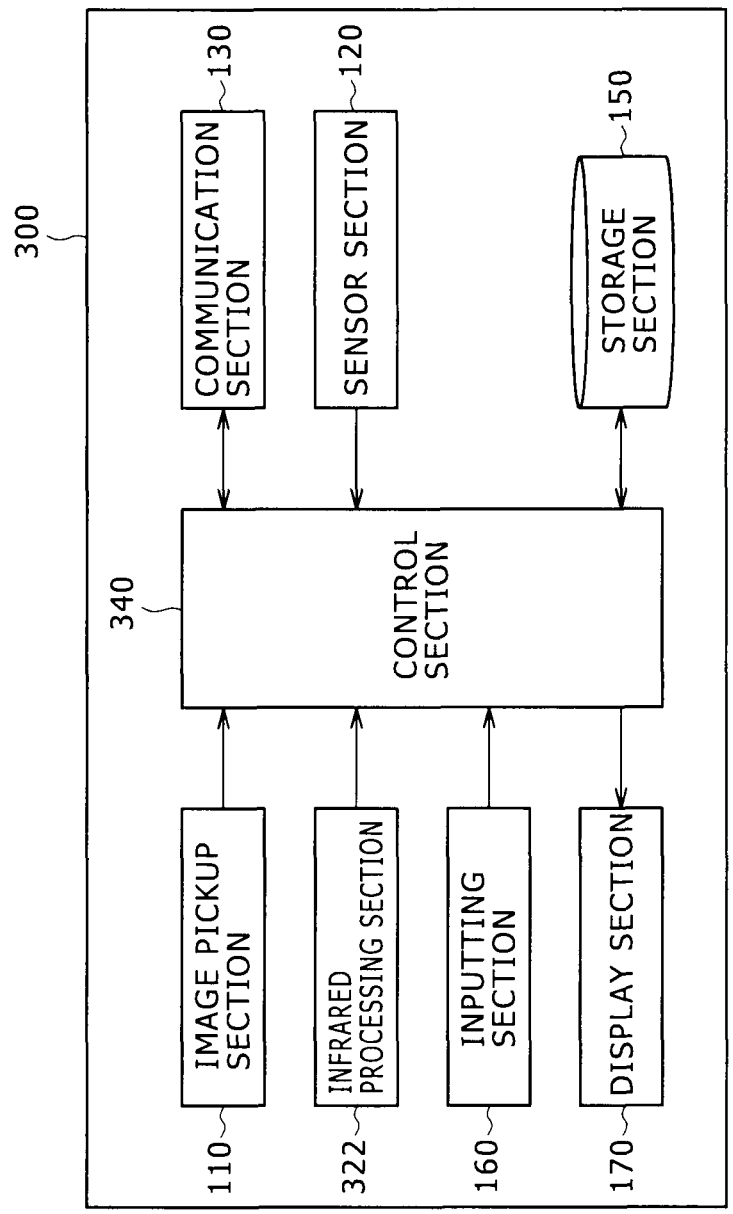
FIG. 14 is a block diagram showing an example of a configuration of the terminal apparatus according to a second embodiment of the present invention.

FIG. 14 shows an example of a configuration of a terminal apparatus 300. Referring to FIG. 14, the terminal apparatus 300 includes an image pickup section 110, a sensor section 120, an infrared processing section 322, a communication section 130, a control section 340, a storage section 150, an inputting section 160 and a display section 170.

Infrared Processing Section

The infrared processing section 322 irradiates near infrared radiations upon food and measures light absorbed by and light reflected from carbohydrates, fats and proteins to detect the quantity of the nutrients and the energy amount included in the food. The infrared processing section 322 may be configured utilizing, for example, a food calorie measuring instrument published in "calorieanswer.com" (online, searched on Mar. 15, 2010, Internet <URL: http://calorieanswer.com/>. The infrared processing section 322 outputs infrared detection data including the values of the detected nutrient quantities and energy amount to the control section 340.

Control Section

The control section 340 controls the whole functions of the terminal apparatus 300 using a control apparatus such as a CPU. For example, if a user input for the instruction of image pickup is detected by the inputting section 160, then the control section 340 instructs the image pickup section 110 to pick up an image and instructs the infrared processing section 322 to irradiate infrared radiations. Further, the control section 340 stores sensor data measured periodically by the sensor section 120 into the storage section 150. Then, the control section 340 transmits an image inputted from the image pickup section 110, infrared detection data inputted from the infrared processing section 322 and sensor data stored in the storage section 150 to an information processing apparatus 400 through the communication section 130. Furthermore, if information transmitted from the information processing apparatus 400 is received by the communication section 130, then the control section 340 controls the display section 170 to display the information.

3-2. Example of the Configuration of the Information Processing Apparatus

Figure 15:
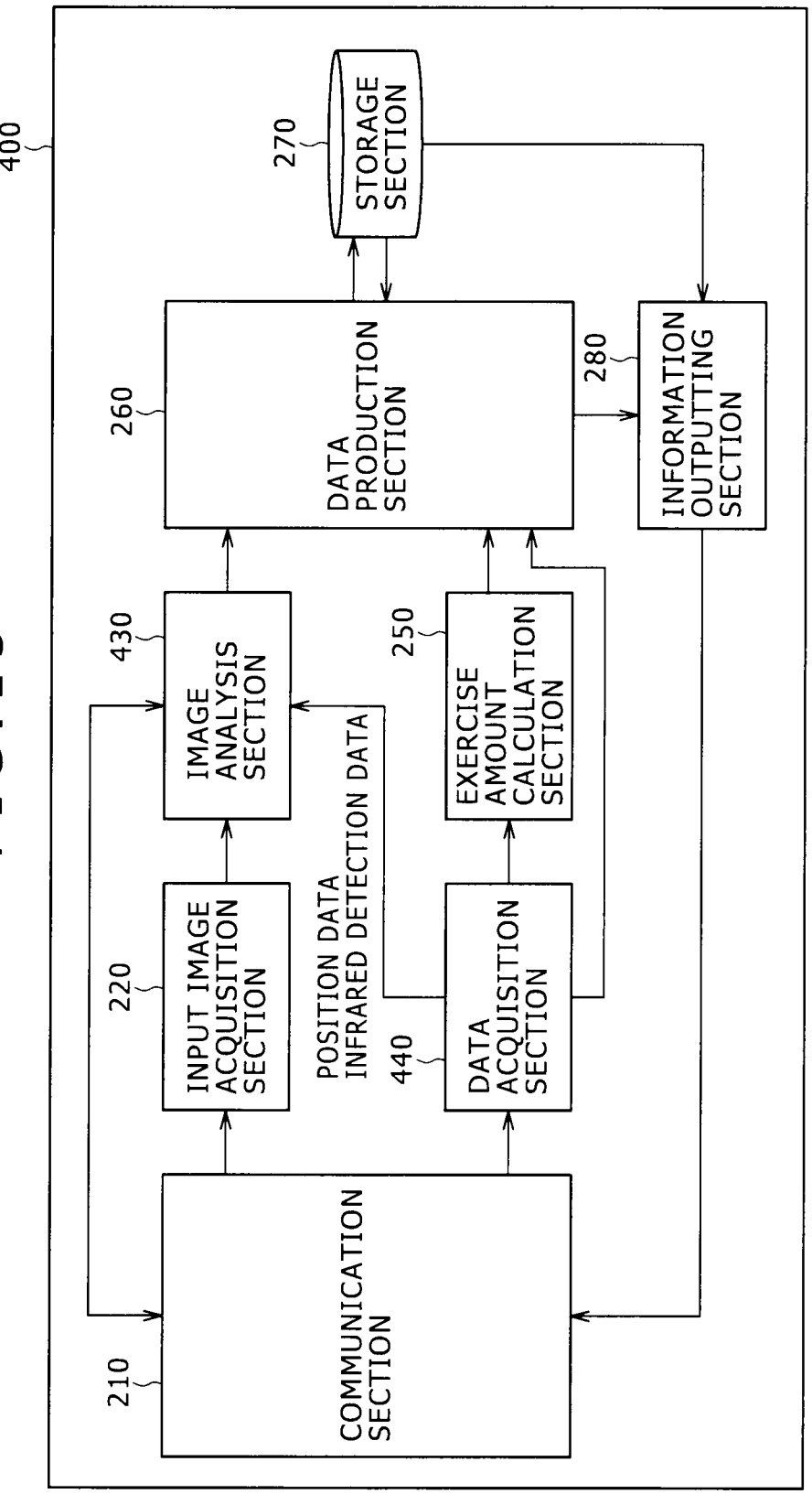
FIG. 15 is a block diagram showing an example of a configuration of an information processing apparatus according to the second embodiment of the present invention.

FIG. 15 shows an example of a configuration of the information processing apparatus 400 according to the present embodiment. Referring to FIG. 15, the information processing apparatus 400 includes a communication section 210, an input image acquisition section 220, an image analysis section 430, a data acquisition section 440, an exercise amount calculation section 250, a data production section 260, a storage section 270 and an information outputting section 280.

Data Acquisition Section

The data acquisition section 440 acquires infrared detection data and sensor data received by the communication section 210 from the terminal apparatus 300. The sensor data acquired by the data acquisition section 440 represent a series of positions, accelerations and body temperatures in a time sequence detected periodically with regard to a user who carries the terminal apparatus 300. Meanwhile, the infrared detection data acquired by the data acquisition section 440 represent the energy of a meal and the quantity of one or more nutrients included in the meal. The data acquisition section 440 outputs the position data and the acceleration data from among the sensor data to the exercise amount calculation section 250. Further, the data acquisition section 440 outputs the living body data such as the body temperatures to the data production section 260. Further, the data acquisition section 440 outputs the position data from among the sensor data to a menu estimation block 434 of the image analysis section 430. Furthermore, the data acquisition section 440 outputs the infrared detection data to a determination block 436 of the image analysis section 430.

Image Analysis Section

Figure 16:
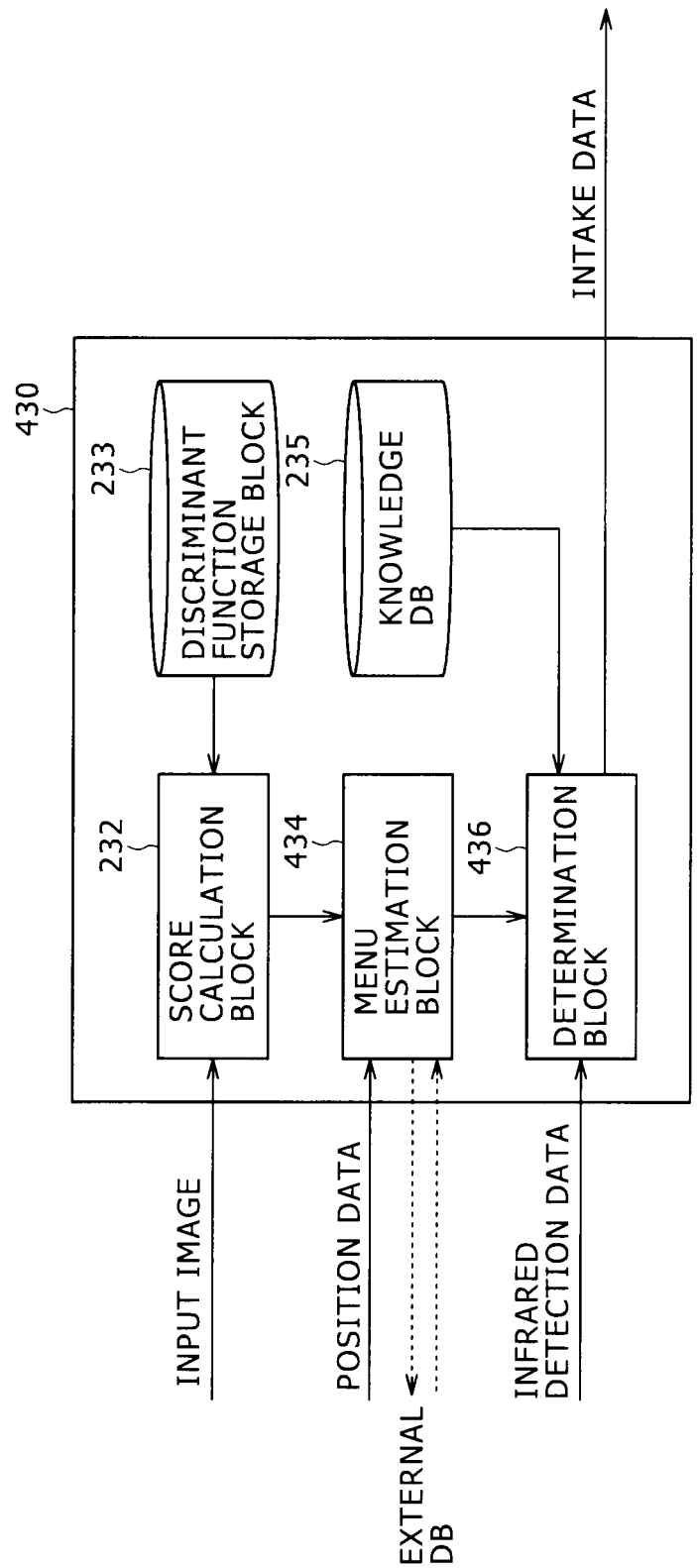
FIG. 16 is a block diagram showing an example of a detailed configuration of an image analysis section shown in FIG. 15.

The image analysis section 430 analyzes an input image acquired by the input image acquisition section 220 to derive the energy of a meal included in the input image and the quantity of one or more nutrients included in the meal. FIG. 16 shows an example of a detailed configuration of the image analysis section 430 in the present embodiment. Referring to FIG. 16, the image analysis section 430 includes a score calculation block 232, a discriminant function storage block 233, a menu estimation block 434, a knowledge database (DB) 235 and a determination block 436.

(1) Menu Estimation Block

The menu estimation block 434 acquires a menu list associated with a position represented by position data inputted from the data acquisition section 440 from an external information source such as a server on the Internet. More particularly, the menu estimation block 434 utilizes, for example, a GPS search function provided by a popular map information service to search for the nearest restaurant to the position indicated by position data at the point of time at which the input image is picked up. Then, the menu estimation block 434 accesses a homepage of the searched out restaurant to acquire a menu list of the restaurant. Then, if the menu estimation block 434 succeeds in the search for the neighboring restaurant and the acquisition of the menu list, then it estimates the menu of the meal included in the input image based on the acquired menu list and by-menu scores calculated by the score calculation block 232.

Figure 17:
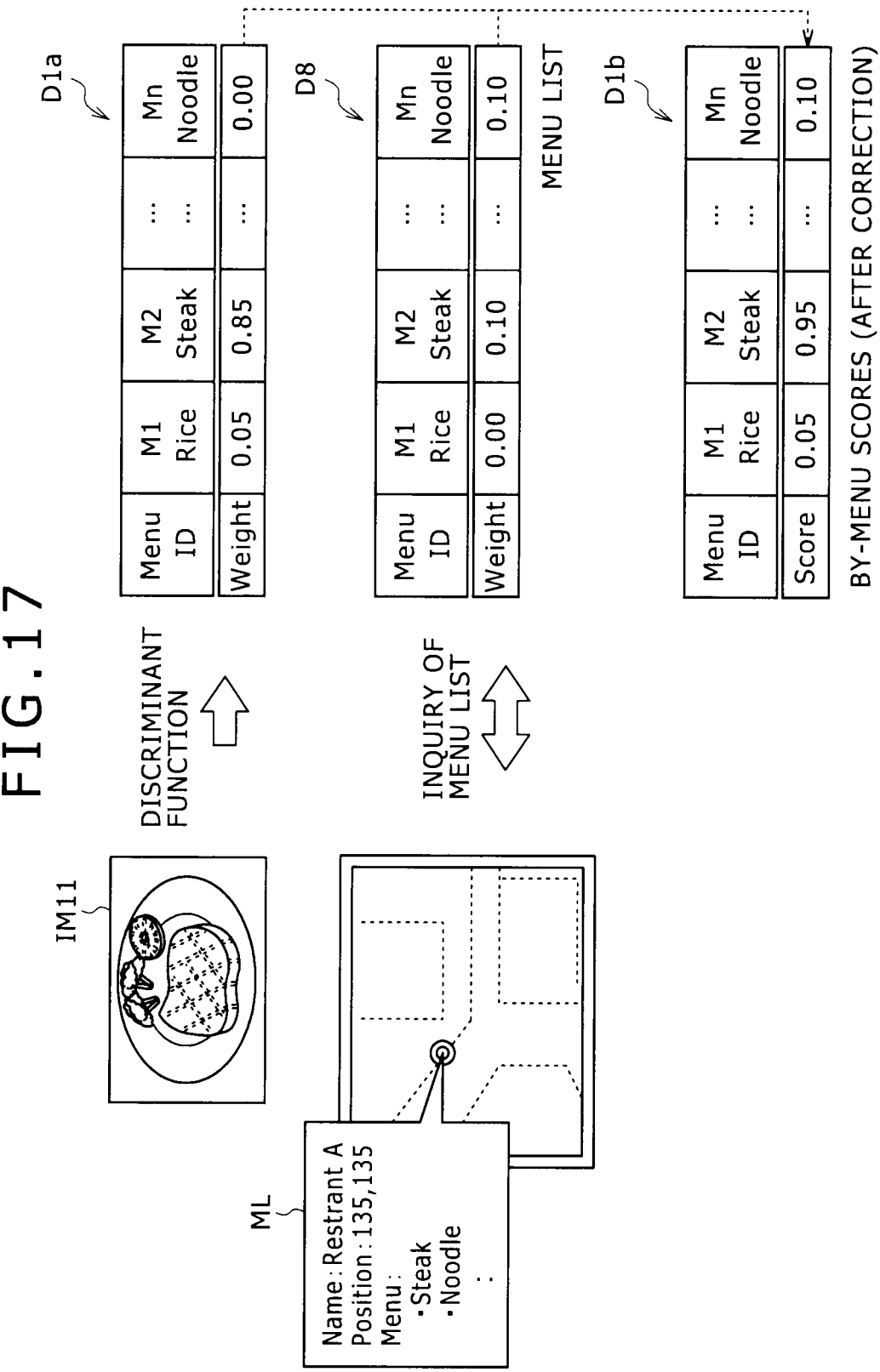
FIG. 17 is a view illustrating a menu estimation process executed by a menu estimation block shown in FIG. 16.

FIG. 17 illustrates a menu estimation process by the menu estimation block 434 in the present embodiment. At an upper state in FIG. 17, by-menu scores D1$a$ calculated by the score calculation block 232 applying a discriminant function to an input image IM are illustrated. In the by-menu scores D1$a$, the score regarding the menu ID=M1 ("Rice") is 0.05, the score regarding the menu ID=M2 ("Steak") is 0.85, and the score regarding the menu ID=Mn ("Noodle") is 0.00. Meanwhile, at a left portion of a meddle stage in FIG. 17, a menu list ML of a restaurant A associated with position data (135, 135) in an external information source is illustrated. The menu list ML includes the steak ("Steak") and the noodle ("Noodle"). Thus, the menu estimation block 434 adds a predetermined weight to values of the by-menu scores D1$a$ regarding the menus included in the menu list ML. In the example of FIG. 17, the value of the weight is 0.10. As a result, by-menu scores D1$b$ after correction are calculated. In the by-menu scores D1$b$ after the correction, the score regarding the menu ID=M1 ("Rice") is 0.05, the score regarding the menu ID=M2 ("Steak") is 0.95, and the score regarding the menu ID=Mn ("Noodle") is 0.10. Then, the menu estimation block 434 estimates that the menu of the meal corresponding to the menu ID whose score is highest in the by-menu scores D1$b$ after the correction is the menu of the meal included in the input image.

It is to be noted that, if the menu estimation block 434 fails in search of a neighboring restaurant or acquisition of a menu list, then it estimates the menu of the meal included in the input image based only on the by-menu scores calculated by the score calculation block 232 similarly to the menu estimation block 234 in the first embodiment.

(2) Determination Block

The determination block 436 uses a nutrition value table of the knowledge DB 235 and infrared detection data inputted from the data acquisition section 440 to determine the values of energy and the quantity of one or more nutrients corresponding to a menu estimated by the menu estimation block 434. The data values determined by the determination block 436 are outputted as intake data representative of the energy and the quantity of nutrients taken in by the user to the data production section 260.

Figure 18:
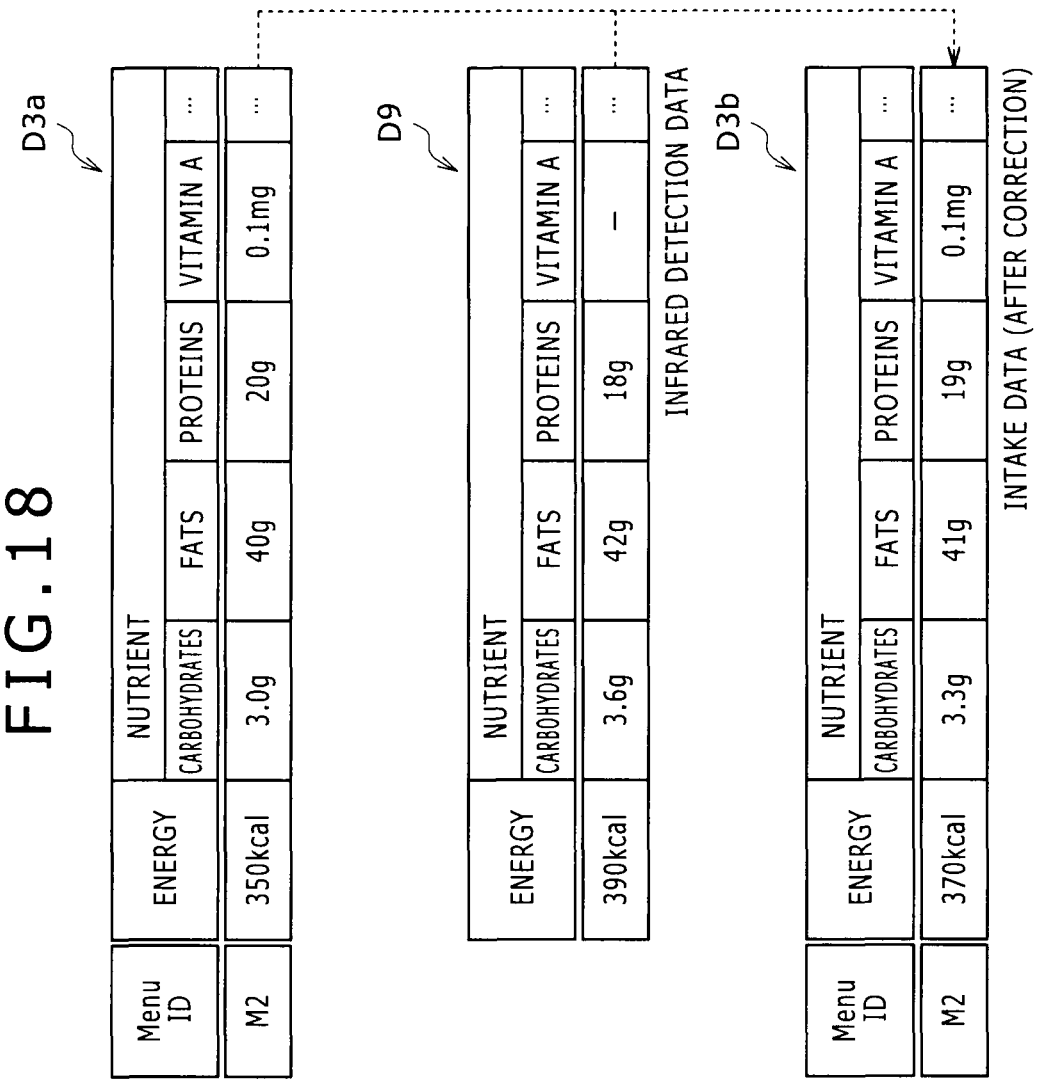
FIG. 18 is a view illustrating an intake data determination process executed by a determination block shown in FIG. 16.

FIG. 18 illustrates an intake data determination process by the determination block 436 in the present embodiment. At an upper stage in FIG. 18, intake data D3$a$ before correction determined by extracting records corresponding to a menu estimated by the menu estimation block 434 from the nutrition value table stored in advance in the knowledge DB 235 as in the intake data determination process in the first embodiment described hereinabove with reference to FIG. 7 are illustrated. In the intake data D3$a$, the energy=350 kcal, carbohydrates 3.0 g, fats=40 g, proteins=20 g and vitamin A=0.1 mg are included. At a middle stage in FIG. 18, infrared detection data D9 as an example inputted from the data acquisition section 440 are illustrated. In the infrared detection data D9, the energy=390 kcal, carbohydrates=3.6 g, fats=42 g, and proteins=18 g are included. It is to be noted that the quantity regarding a nutrient such as vitamin A which cannot be detected using infrared radiations is not included in the infrared detection data D9. The determination block 436 calculates an average value of the data values regarding the energy and the nutrients having data items in both of the intake data D1$a$ and the infrared detection data D9 to determine intake data D3$b$ after correction. At a lower stage in FIG. 18, the intake data D3$b$ after the correction are illustrated. In the intake data D3$b$ after the correction, the energy=370 kcal, carbohydrates=3.3 g, fats=41 g, proteins=19 g and vitamin A=0.1 mg are included.

In this manner, in the present embodiment, position data and infrared detection data of the terminal apparatus 300 are used supplementally as information other than an input image to correct the value of intake data which configure life data. It is to be noted that, as another mode, only one of the position data and the infrared detection data may be used to correct the value of intake data which configure by-menu scores or life data.

3-3. Flow of Processing

A flow of an information outputting process by the information processing apparatus 400 according to the present embodiment may be similar to the flow of the information outputting process by the information processing apparatus 200 according to the first embodiment described hereinabove with reference to FIG. 12.

Figure 19:
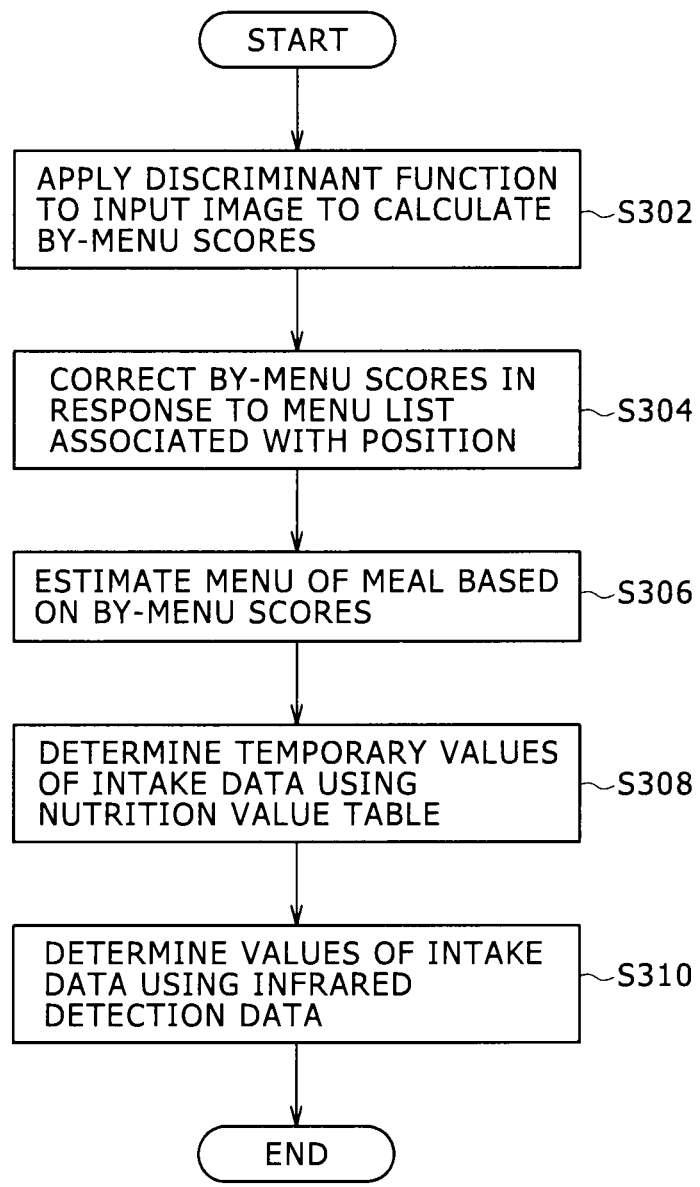
FIG. 19 is a flow chart illustrating an example of a flow of an image analysis process executed by the image analysis section of FIG. 16.

FIG. 19 illustrates an example of a flow of an image analysis process by the image analysis section 430 of the information processing apparatus 400 according to the present embodiment.

Referring to FIG. 19, the score calculation block 232 of the image analysis section 430 first applies a discriminant function acquired by a learning process in advance to an input image to calculate by-menu scores at step S302. Then, the menu estimation block 434 corrects the by-menu scores calculated by the score calculation block 232 in accordance with a menu list associated with the position of the terminal apparatus 300 represented by position data inputted from the data acquisition section 440 at step S304. Then, the menu estimation block 434 estimates a menu of a meal included in the input image based on the by-menu scores after the correction at step S306. Then, the determination block 436 searches records of a nutrition value table corresponding to the menu estimated by the menu estimation block 434 to determine temporary values of intake data regarding the menu of the meal included in the input image at step S308. Then, the determination block 436 uses infrared detection data inputted from the data acquisition section 440 to correct the temporary values of the intake data at step S310.

The information outputting section 280 of the information processing apparatus 400 outputs information including an advice to the user of the terminal apparatus 300 based on comparison between life data including the intake data corrected in this manner and the model data.

3-4. Summary of the Second Embodiment

The second embodiment of the present embodiment has been described with reference to FIGS. 14 to 19. According to the present embodiment, an advice regarding eating habits is provided to the user based on comparison between model data representative of target values regarding the energy of a meal, the quantity of one or more nutrients included in the meal and the amount of exercise and life data including a result of analysis of a picked up input image of the substance of the meal and the amount of exercise by the user. Then, upon determination of intake data which configure the life data, a menu list associated with the position of the user is acquired from an external information source, and the menu list is used supplementally to estimate the menu of the meal. Consequently, the accuracy in estimation of a menu is improved. Further, in the present embodiment, intake data which configure the life data are corrected using the values of the energy of the meal and the quantity of one or more nutrients included in the meal detected using infrared radiations irradiated upon the meal. As a result, the accuracy of the intake data among the life data representative of the tendency of the eating habits of the user is improved. Accordingly, with the present embodiment, an advice regarding eating habits based on comparison between the life data of the improved accuracy and the model data can be provided to the user.

It is to be noted that the series of processes in each embodiment described hereinabove is implemented typically using software. A program which configures the software for implementing the series of processes is stored in advance in or on a storage medium provided inside or outside each apparatus. Then, the program is read, for example, upon execution thereof, into a RAM (Random Access Memory) of each apparatus and executed by a processor such as a CPU.

Further, in the present specification, description is given principally of an example wherein the terminal apparatus 100 or 300 and the information processing apparatus 200 or 400 are different from each other. However, it is apparent that, for example, the terminal apparatus 100 and the information processing apparatus 200, or the terminal apparatus 300 and the information processing apparatus 400, may be implemented as a physically single apparatus having the functions of them within the scope of the present invention.

While preferred embodiments of the present invention have been described using specific terms, such description is for illustrative purpose only, and it is to be understood that changes and variations may be made without departing from the spirit or scope of the following claims.

The present application contains subject matter related to that disclosed in Japanese Priority Patent Application JP 2010-087784 filed in the Japan Patent Office on Apr. 6, 2010, the entire content of which is hereby incorporated by reference.

What is claimed is:

1. A computer comprising:
an interface configured to acquire an image, said image including at least part of a meal; and
an image analysis mechanism configured to analyze the image using a discriminant function of discriminating the content of a meal from the image of the at least part of the meal, and to recognize a property of the at least part of the meal, said property including at least one of an energy and a quantity of one or more nutrients associated with the at least part of a meal,
the image analysis mechanism further being configured to assign a score for said property to the at least part of the meal based on the discriminant function,
wherein said image analysis mechanism is further configured to receive at least one of an image of a menu or a text-based version of said menu to assist the image analysis mechanism in recognizing the property.

2. The computer of claim 1, further comprising:
a generation unit configured to generate display information upon which an analysis result is displayed, said analysis result including at least one of an activity recommendation, a nutrient recommendation and at least part of a meal recommendation based on the property of the at least part of a meal.

3. The computer of claim 1, wherein:
said processor is configured to perform a comparison of a health management model with said property of the at least part of a meal and exercise data and produce at least one of activity recommendation, a nutrient recommendation and at least part of a meal recommendation based on said comparison, said health management model having at least a property of a part of a meal component and an exercise component.

4. The computer of claim 1, wherein
said image analysis mechanism is configured to receive data describing a location of a terminal that sends said image of the at least a part of the meal to assist the image analysis mechanism in recognizing the property.

5. The computer of claim 1, wherein said image analysis mechanism includes an infrared processing section.

6. An apparatus comprising:
a non-transitory computer readable storage device configured to store therein computer readable instructions; and
a processor configured to acquire an image of at least a part of a meal and when said processor executes said computer readable instructions, said processor sends a request to another device for analyzing the image using a discriminant function of discriminating the content of a meal from the image of the at least part of the meal, to recognize a property of the at least part of a meal,
said property including at least one of an energy and a quantity of one or more nutrients associated with the at least part of a meal,
wherein the processor is further configured to assign a score for said property to the at least part of the meal based on the discriminant function.

7. The apparatus of claim 6, further comprising:
a communication interface through which said processor sends said request, and through which said processor receives an analysis result from said another device; and
a display upon which said analysis result is displayed, said analysis result including at least one of an activity recommendation, a nutrient recommendation and at least part of a meal recommendation based on the property of the at least part of a meal.

8. The apparatus of claim 7, wherein said at least one of said activity recommendation, said nutrient recommendation and said at least part of a meal recommendation is based on a comparison of the property of the at least part of a meal and exercise data against a predetermined health management model.

9. The apparatus of claim 6, further comprising:
at least one of a heart rate monitor, a pedometer and an accelerometer configured to monitor accumulated exercise data.

10. The apparatus of claim 6, wherein:
said communication interface is configured to receive a wireless signal input from at least one of a heart rate monitor, a pedometer and an accelerometer as input regarding user exercise.

11. The apparatus of claim 6, wherein:
said processor also sends at least one of an image of a menu and a text-based version of said menu to said another device for facilitating in the analyzing the image.

12. The apparatus of claim 6, further comprising:
a location detector configured to detect a location of said apparatus when said image of the at least a part of the meal is sent to said another device for facilitating said another device in determining a menu of food items available at eating establishments near said location.

13. A non-transitory computer readable storage device, comprising:
- an interface configured to receive and store therein downloaded instructions, said downloaded instructions when executed by a computer processor perform a method including
- acquiring an image of at least a part of a meal; and
- analyzing with the computer processor the image using a discriminant function of discriminating the content of a meal from the image of the at least part of meal, to recognize a property of the at least part of the meal, said property including at least one of an energy and a quantity of one or more nutrients associated with the at least part of a meal,
- wherein the analyzing step includes assigning a score for said property to the at least part of the meal based on the discriminant function.

14. The non-transitory computer readable storage device of claim 13, wherein said analyzing includes
- sending a wireless message to another device of the image to recognize the property of the at least part of a meal, and
- receiving an analysis result from said another device.

15. The non-transitory computer readable storage device of claim 13, wherein the method performed by the processor further comprising:
- using at least one of location information and menu information to assist in said analyzing.

16. The non-transitory computer readable storage device of claim 13, wherein the method performed by the processor further comprising:
- including accumulated exercise information in said analyzing step; and
- presenting on a display at least one of a nutrition advice message, a recommended exercise message, and at least part of a meal recommendation based on said analysis result.

17. A method for analyzing at least part of a meal, comprising:
- acquiring an image of at least part of a meal; and
- analyzing with a computer processor the image using a discriminant function of discriminating the content of a meal from an image of the at least part of the meal, to recognize a property of the at least part of the meal as a factor in an analysis result, said property including at least one of an energy and a quantity of one or more nutrients associated with the at least part of a meal,
- wherein the image analyzing step includes assigning a score for said property to the at least part of the meal based on the discriminant function.

18. The method of claim 17, wherein:
said analyzing includes
- including accumulated exercise data as another factor in said analysis result, and
- comparing said accumulated exercise data and said property of the at least part of a meal to a predetermined health management model.

19. The method of claim 18, further comprising:
sensing at least a portion of accumulated exercise data with at least one of a heart rate monitor, a pedometer and an accelerometer.

* * * * *